(12) United States Patent
Scadden et al.

(10) Patent No.: US 7,943,136 B2
(45) Date of Patent: *May 17, 2011

(54) PARATHYROID HORMONE RECEPTOR ACTIVATION AND STEM AND PROGENITOR CELL EXPANSION

(75) Inventors: David T. Scadden, Weston, MA (US); Laura M. Calvi, Rochester, NY (US); Gregor Adams, Boston, MA (US); Henry M. Kronenberg, Belmont, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/621,325

(22) Filed: Nov. 18, 2009

(65) Prior Publication Data

US 2010/0113360 A1 May 6, 2010

Related U.S. Application Data

(60) Division of application No. 11/268,971, filed on Nov. 8, 2005, now Pat. No. 7,635,477, which is a continuation-in-part of application No. 10/521,971, filed as application No. PCT/US03/023425 on Jul. 25, 2003, now Pat. No. 7,429,383.

(60) Provisional application No. 60/398,801, filed on Jul. 25, 2002, provisional application No. 60/648,216, filed on Jan. 28, 2005, provisional application No. 60/626,671, filed on Nov. 11, 2004.

(51) Int. Cl.
*A61K 39/00* (2006.01)
*A61K 39/38* (2006.01)
*A61K 35/26* (2006.01)

(52) U.S. Cl. .................................... 424/184.1; 424/577

(58) Field of Classification Search ........................ None
See application file for complete search history.

(56) References Cited

U.S. PATENT DOCUMENTS

| | | | |
|---|---|---|---|
| 5,061,620 A | 10/1991 | Tsukamoto et al. | |
| 5,747,456 A | 5/1998 | Chorev et al. | |
| 6,316,410 B1 | 11/2001 | Barbier et al. | |
| 6,342,477 B1 | 1/2002 | Tamura et al. | |
| 6,956,022 B2 | 10/2005 | Tamura et al. | |
| 7,429,383 B2* | 9/2008 | Scadden et al. | 424/184.1 |
| 7,635,477 B2* | 12/2009 | Scadden et al. | 424/184.1 |
| 2005/0197296 A1 | 9/2005 | Tamura et al. | |
| 2006/0257376 A1 | 11/2006 | Scadden et al. | |

FOREIGN PATENT DOCUMENTS

| | | |
|---|---|---|
| WO | WO 00/70022 | 11/2000 |
| WO | WO 2001/12785 | 2/2001 |
| WO | WO 2004/011484 | 2/2004 |

OTHER PUBLICATIONS

Nilsson, et al., "Spatial localization of transplanted hemopoietic stem cells: inferences for the localization of stem cell niches." Blood, 97:2293-2299 (2001).
Peled et al., "Dependence of Human Stem Cell Engraftment and Repopulation of NOD/SCID Mice on CXCR4." Science, 283:845-8 (1999).
Rood et al., "Adhesion of hematopoietic progenitor cells to human bone marrow or umbilical vein derived endothelial cell lines: A comparison." Exp. Hematol., 27:1306-14 (1999).
Su et al., "Inhibition of Tyrosine Kinase Activation Blocks the Down-Regulation of CXC Chemokine Receptor 4 by HIV-1 gp120 in CD4+ T Cells." J Immunol., 162:7128-7132 (1999).
Taichman et al., "Hepatocyte growth factor is secreted by osteoblasts and cooperatively permits the survival of haematopoietic progenitors." Br. J. Haematol., 112:438-448 (2001).
Taichman at al., "Human Osteoblasts Support Human Hematopoietic Progenitor Cells in In Vitro Bone Marrow Cultures." Blood, 87:518-524 (1996).
Supplementary European Search Report issued in EP 05851439,9, Mar. 6, 2009, The General Hospital Corporation.
Extended European Search Report issued in EP 05851439,9, Mar. 16, 2009, The General Hospital Corporation.
Taichman et al., "Human Osteoblasts Support Hematopoiesis through the Production of Granulocyte Colony-stimulating Factor." J. Exp. Med., 179:1677-1682 (1994).
Taichman et al., "The Role of Osteoblasts in the Hematopoietic Microenvironment." Stem Cells, 16:7-15 (1998).
Theise et al., "Liver from Bone Marrow in Humans." Hepatology 32, 11-6 (2000).
Teitelbaum et al., "Bone Resorption by Osteoclasts." Science, 289:1504-1508 (2000).
Van Der Loo et al., "VLA-5 Is Expressed by Mouse and Human Long-term Repopulating Hematopoietic Cells and Mediates Adhesion to Extracellular Matrix Protein Fibronectin." J. Clin. Invest. 102:1051-61 (1998).
Zanjani et al., "Homing of Human Cells in the Fetal Sheep Model: Modulation by Antibodies Activating or Inhibiting Very Late Activation Antigen-4-Dependent Function." Blood, 94:2515-22 (1999).
Zou et al., "Function of the chemokine receptor CZCR4 in haematopoiesis and in cerebellar development." Nature, 393:595-9 (1998).
Choi, "Hemangioblast development and regulation." Biochem Cell Biol 76, 947-56 (1998).
Cui et al., "The relative spatial distribution of in vitro-CFC's in the bone marrow, responding to specific growth factors." Cell Prolif., 29:243-257 (1996).
Ducy, et al.,"The Osteoblast: A sophisticated Fibroblast under Central Surveillance." Science, 289:1501-1504 (2000).

(Continued)

*Primary Examiner* — Michail A Belyavskyi
(74) *Attorney, Agent, or Firm* — Edwards Angell Palmer & Dodge LLP; Peter C. Lauro, Esq.; Elbert Chiang

(57) ABSTRACT

The invention relates to methods for manipulating hematopoietic stem or progenitor cells, mesenchymal stem cells, epithelial stem cells, neural stem cells and related products through activation of the PTH/PTHrP receptor in neighboring cells.

14 Claims, 16 Drawing Sheets

OTHER PUBLICATIONS

Eglitis et al., "Hematopoietic cells differentiate into both microglia and macroglia in the brains of adult mice." Proc Natl Acad Sci U S A 94, 4080-5 (1997).

Gong et al., "Endosteal Marrow: A Rich Source of Hematopoietic Stem Cells." Science, 199:1443-1445 (1978).

Greenberg et al., "Relationship between selectin-mediated rolling of hematopoietic stem and progenitor cells and progression in hematopoietic development." Blood, 95:478-86 (2000).

Gussoni et al., "Dystrophin expression in the mdx mouse restored by stem cell transplantation." Nature 401, 390-4 (1999).

Lord et al., "The Relative Spatial Distributions of $CFU_s$ and $CFU_c$ in the Normal Mouse Femur." Blood, 46:65-72 (1975).

Ma et al., "The Chemokine Receptor CXCR4 is Required for the Retention of B Lineage and Granulocytic Precursors within the Bone Marrow Microenvironment." Immunity, 10:463-71 (1999).

Nagasawa et al., "Defects of B-cell lymphopoiesis and bone-marrow myelopoiesis in mice lacking the CXC chemokine PBSF/SDF-1." Nature, 382:635-8 (1996).

Lord et al., Int. J. Cell Clon., 8:317-331 (1990).

Whitfield, J.F., et al. "Parathyroid Hormone, Its Fragments and Their Analogs for the Treatement of Osteoporosis" *ADIS International* 1(3): 175-190 (Jan. 1, 2002).

Naiyer et al., "Stromal Derived Factor-1-Induced Chemokinesis of Cord Blood CD34+ Cells (Long-Term Culture-Initiating Cells) Through Endothelial Cells Is mediated by E-Selection." Blood, 94:4011-9 (1999).

Calvi et al. "Activated parathyroid hormone/parathyroid hormone-related protein receptor in osteoblastic cells differentially affects cortical and trabecular bone" *The Journal of Clinical Investigation*, (2001) 107, No. 3, 277-286.

Fuller et al. "Induction of oesteoclast formation by parathyroid hormone depends on an action on stromal cells", *Journal of Endocrinology* (1998) 158, 341-350.

Hollnagel et al. "Parathyroid Hormone Enhances Early and Suppresses Late Stages of Osteogenic and Chondrogenic Development in a BMP-Dependent Mesenchymal Differentiation System (C3H10T1/2)", *Journal of Bone and Mineral Research*, 1997, 12(12): 1993-2004.

Liu et al. "Conditionally Immortalized Murine Bone Marrow Stromal Cells Mediate Parathyroid Hormone-Dependent Osteoclastogenesis in Vitro*'", *Endocrinology* (1998) 139, No. 4, pp. 1952-1964.

Whitfield, J.F., "Parathyroid Hormone (PTH) and Hematopoiesis: New Support for Some Old Observations," *Journal of Cellular Biochemistry*, 2005, 96: 278-284.

Williams et al., "Fibronectin and VLA-4 in haematopoietic stem cell-microenvironment interactions," *Nature*, 1991, 352: 438-441.

Forteo Definition and Product Information from Physicians' Desk Reference (2004) 58 Edition pp. 1808-1812.

Adams et al. "Interaction of Bone and Bone Marrow: Expansion of Hematopoietic Stem Cells In Vivo and In Vitro through Activation of the PTH/PTHrP Receptor in Bone Marrow Stromal Cells" Blood 100(11) 501 (2002) Abstract only.

Shevde et al. "Stromal Cell-Mediated Stimulation of Osteoclasogenesis" Proceedings of the Scoiety for Experimental Biology and Medicine, Academic Press Inc. 205(4) 306-315 (1994).

Liang et al. "Immunohistochemical Localization of Selected Early Response Genes Expressed in Trabecular Bone of Young Rats Given hPTH 1-34" Calcif Tissue Int. 65: 369-373 (1999).

Rixon et al. "Increased Survival of Rats irradiated with X-Rays and treated with Parathyroid Extract" Nature 182(4646): 1374 (1958).

Gallien-Lartigue et al. "In Vitro induction of the S phase in multipotent stem cells of bone marrow by parathyroid hormone"C. R.Acad. Sci. 278(13): 1765-1768 (1974).

Anklesaria et al. "Engraftment of a clonal bone marrow stromal cell line in vivo stimulates hematopoietic recovery from total body irradiation" Proc. Natl. Acad. Sci USA 84: 7681-7685 (1987).

Collins et al. "A Stromal Cell Line from Myeloid Long-Term Bone Marrow Cultures can Support Myelopoiesis and B Lymphopoiesis" J. of Immunol. 138: 1082-1087 (1987).

Luck et al. "The (1-14) Fragment of Parathyroid Hormone (PTH) Activates Intact and Amino-Terminally Truncated PTH-1 Receptors" Molecular Endocrinology 13(5): 670-680 (1999).

Calvi et al. "Osteoblastic cells regulate the haematopoietic stem cell niche" Nature 23, Oct. 2003, vol. 25, Nature Publishing Group, pp. 841-846.

Old Observations. J of Cell Biochem. 96:278-284 (2005).

* cited by examiner

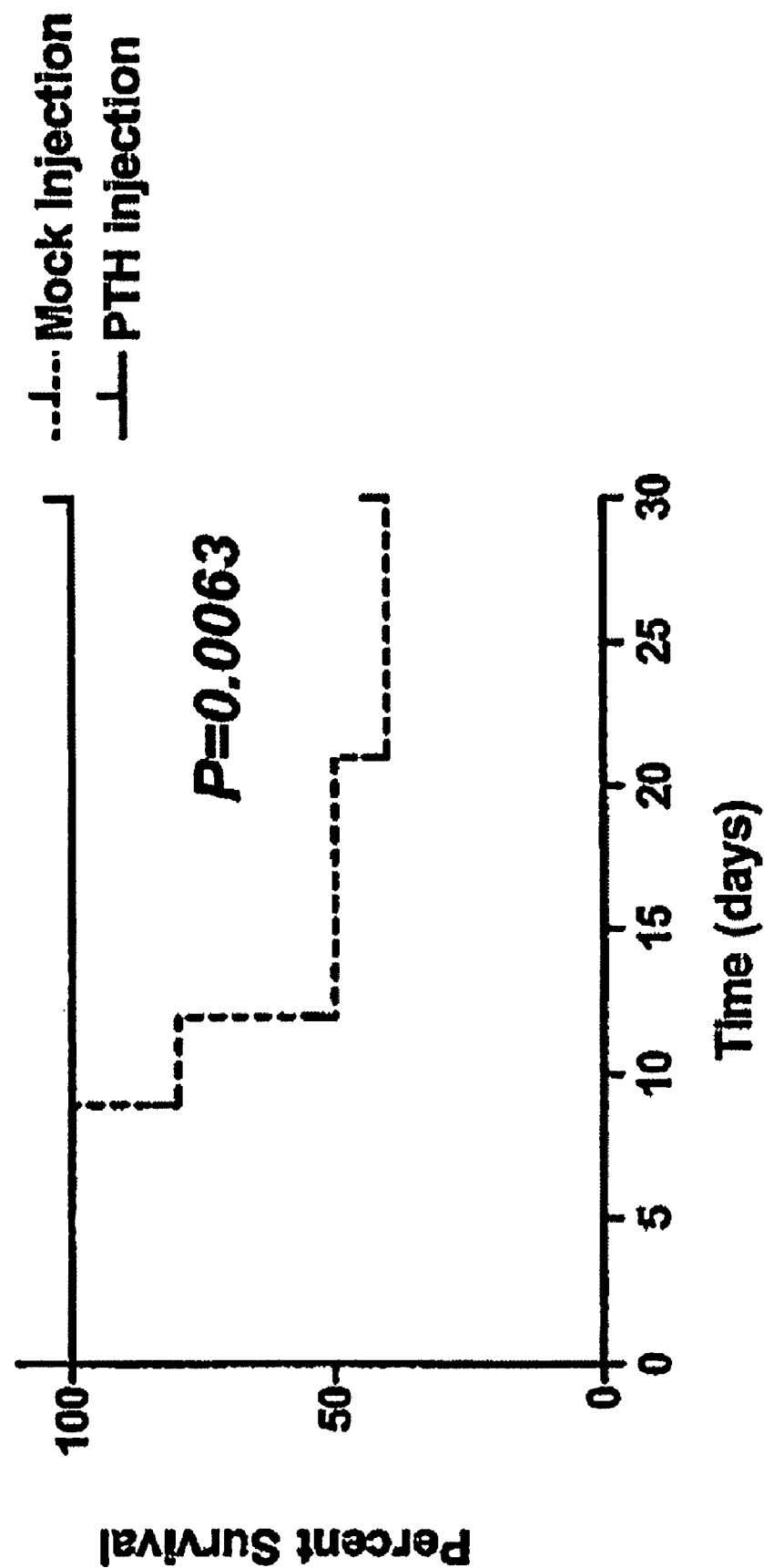

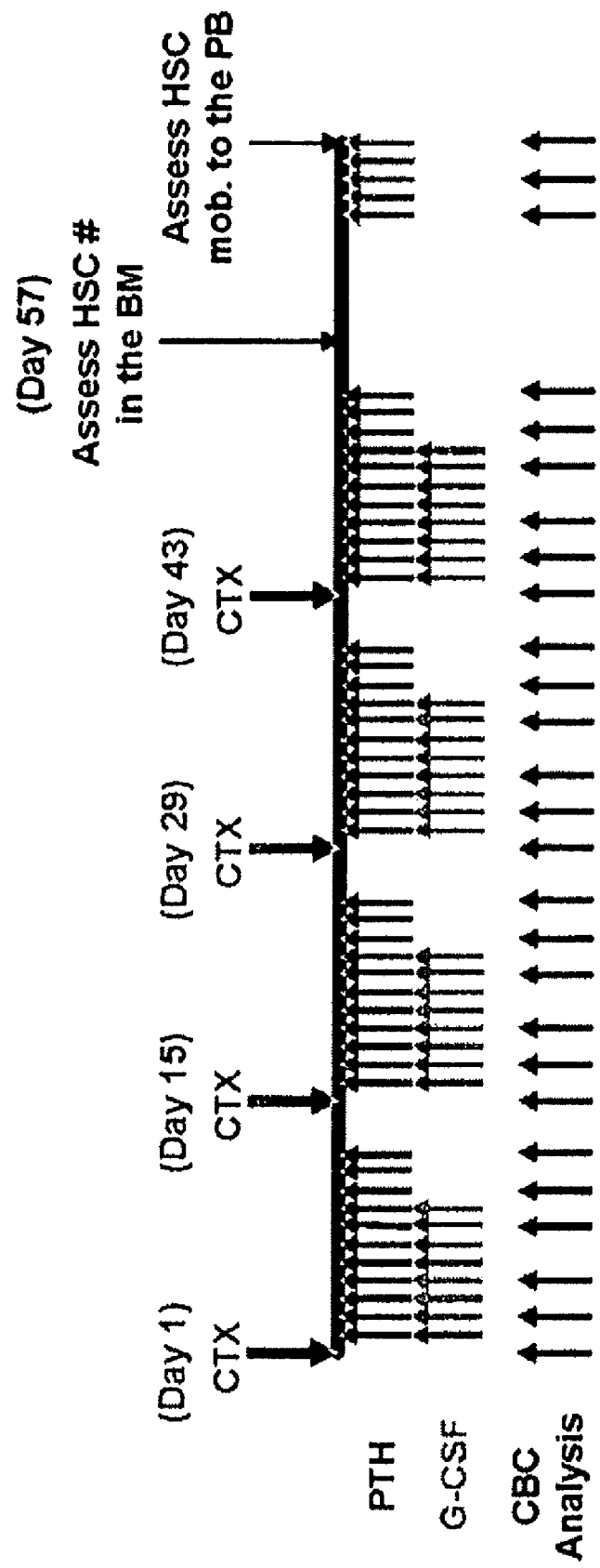

H₂N-Ser-Val-Ser-Glu-Ile-Gln-Leu-Met-His-Asn-Leu-Gly-Lys-His-Leu-Asn-Ser-Met-Glu-Arg-
Val-Glu-Trp-Leu-Arg-Lys-Leu-Leu-Gln-Asp-Val-NH₂

FIG. 8

FIG. 13A
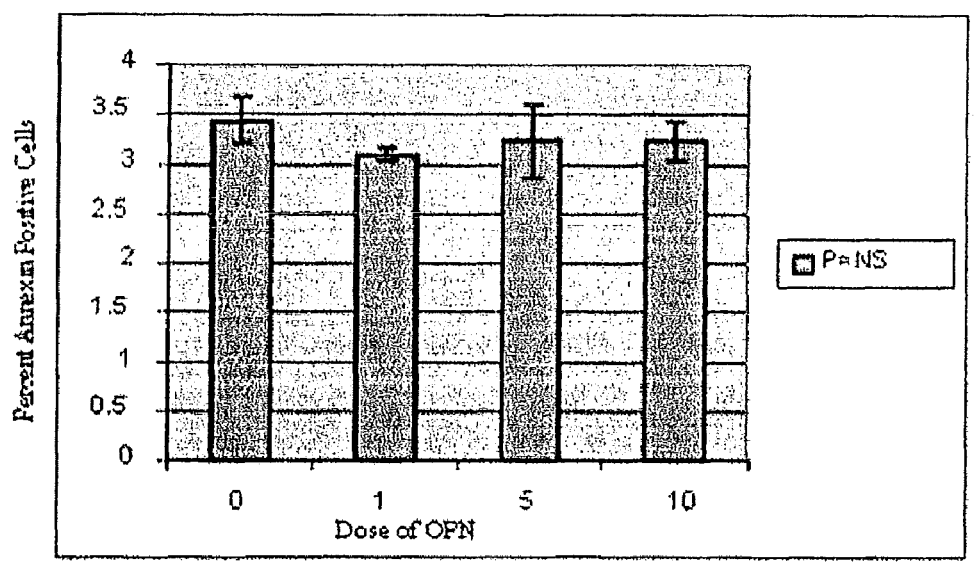
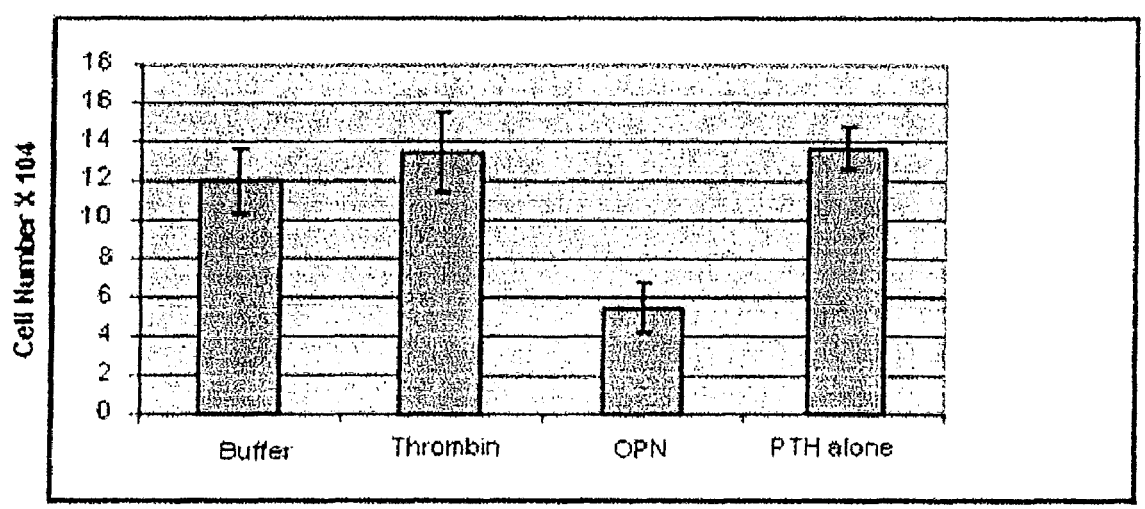
FIG. 13B

SEQUENCE LISTING

```
<160> NUMBER OF SEQ ID NOS: 3

<210> SEQ ID NO 1
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Val Ser Glu Ile Gln Leu Met His Asn Leu Gly Lys His Leu Asn
 1               5                   10                  15

Ser Met Glu Arg Val Glu Trp Leu Arg Lys Leu Leu Gln Asp Val
            20                  25                  30

<210> SEQ ID NO 2
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
taatacgact cactataggg cgataaacaa gttaacaaca acaat             45
```

```
<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctttgtgaag gaaccttact                                                   20
```

PARATHYROID HORMONE RECEPTOR ACTIVATION AND STEM AND PROGENITOR CELL EXPANSION

CROSS-REFERENCE TO RELATED APPLICATIONS

This application is a divisional application of U.S. application Ser. No. 11/268,971, filed on Nov. 8, 2005, now U.S. Pat. No. 7,635,477, issued on Dec. 22, 2009, which is a continuation-in-part of U.S. application Ser. No. 10/521,971, filed on Sep. 26, 2005, now U.S. Pat. No. 7,429,383, issued on Sep. 30, 2008, which claims priority to International Application No. PCT/US03/023425, filed Jul. 25, 2003, which claims priority to U.S. Provisional Application Ser. No. 60/398,801, filed Jul. 25, 2002, the contents each of which are expressly incorporated herein by reference. This application also claims priority to U.S. Provisional Application Ser. No. 60/648,216, filed on Jan. 28, 2005 and U.S. Provisional Application Ser. No. 60/626,671, filed Nov. 11, 2004, the contents each of which are expressly incorporated herein by reference.

Each of the applications and patents cited in this text, as well as documents or references cited in each of the applications and patents (including during the prosecution of each issued patent; "application cited document") and each of the PCT and foreign applications and patents, and each of the documents cited or referenced in each of the application cited documents, are hereby expressly incorporated herein by reference, and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference. Documents incorporated by reference into this text or any teaching therein can be used in the practice of this invention.

GOVERNMENT SUPPORT

The work leading to the present invention was funded in part by contract/grant numbers HL65909, CA86355, DK60317, and AR44855, from the United States National Institutes of Health. Accordingly, the United States Government has certain rights to this invention.

BACKGROUND OF THE INVENTION

Circulating blood cells, such as erythrocytes, leukocytes, platelets and lymphocytes, arise from the terminal differentiation of precursor cells, in a process referred to as hematopoiesis. In fetal life, hematopoiesis occurs throughout the reticular endothelial system. In the normal adult, terminal differentiation of the precursor cells occurs exclusively in the marrow cavities of the axial skeleton, with some extension into the proximal femora and humeri. These precursor cells, in turn, derive from immature cells, called progenitors, stem cells or hematopoietic cells.

Hematopoietic progenitor cells have therapeutic potential as a result of their capacity to restore blood and immune cell function in transplant recipients as well as their potential ability to generate cells for other tissues such as brain, muscle and liver (Choi, 1998 Biochem Cell Biol 76, 947-56; Eglitis and Mezey, 1997 Proc Natl Acad Sci USA 94, 4080-5; Gussoni et al., 1999 Nature 401, 390-4; Theise et al., 2000 Hepatology 32, 11-6). Human autologous and allogeneic bone marrow transplantation methods are currently used as therapies for diseases such as leukemia, lymphoma, and other life-threatening diseases. For these procedures a large amount of donor bone marrow must be isolated to ensure that there are enough cells for engraftment. Hematopoietic progenitor cell expansion for bone marrow transplantation is a potential method for generating human long-term bone marrow cultures for these therapeutic utilities. Several studies have reported the isolation and purification of hematopoietic progenitor cells (see, e.g., U.S. Pat. No. 5,061,620), but none of these methods have been overwhelmingly successful.

Determining the basis for progenitor cell localization is important to maximizing the therapeutic potential of those cells. During development, hematopoiesis translocates from the fetal liver to the bone marrow, which then remains the site of hematopoiesis throughout adulthood. Once hematopoiesis has been established in the bone marrow, the hematopoietic progenitor cells are not distributed randomly throughout the bone cavity. Instead, the hematopoietic progenitor cells are found in close proximity to the endosteal surfaces (Lord et al., 1975, Blood, 46:65-72; Gong et al., 1978, Science, 199:1443-1445), an observation recently confirmed when injected purified hematopoietic progenitor cells were found to preferentially localize to the endosteal surfaces approximately 10 hours following injection (Nilsson, et al., 2001, Blood, 97:2293-2299). The more mature progenitor cells (as measured by their CFU-C activity) increased in number as the distance from the bone surface increased. Finally, as the central longitudinal axis of the bone is approached, it has been shown that terminal differentiation of mature cells occurs (Lord et al., 1975, Blood, 46:65-72; Cui et al., 1996, Cell Prolif., 29:243-257; Lord et al., 1990, Int. J. Cell Clon., 8:317-331).

Given the relationship between the hematopoietic progenitor cells and the endosteal surfaces of the bone, one cell type that has been implicated in playing a role in hematopoiesis is the osteoblast (Taichman and Emerson, 1998, Stem Cells, 16:7-15). Osteoblastic cells are skeletal cells responsible for the production and mineralization of bone matrix, in response to local and hormonal stimuli (Ducy, et al., 2000, Science, 289:1501-1504). In addition, these cells regulate bone remodeling by modulating the formation and activity of osteoclasts, bone-resorbing cells of hematopoietic origin, through the RANK/RANK-Ligand system (Teitelbaum et al., 2000, Science, 289:1504-1508). Studies have demonstrated that osteoblastic cells can support the growth of primitive hematopoietic cells, through the release of G-CSF and other growth factors (Taichman and Emerson, 1994, J. Exp. Med., 179:1677-1682; Taichman et al., 1996, Blood, 87:518-524; Taichman et al., 2001, Br. J. Haematol., 112:438-448).

The ability to manipulate progenitor cells could improve the efficiency of engraftment of transplanted cells. Currently, transplantation techniques are extremely inefficient. In view of their enormous therapeutic potential relatively little is known about how hematopoietic progenitor cells are regulated, e.g., what factors cause cell localization, expansion, etc. Some studies have suggested that progenitor cell localization into the bone marrow space is chemokine dependent. For instance, the absence of either SDF-1 or its receptor, CXCR-4, was found to preclude localization of hematopoiesis in the bone marrow in developing mice (Nagasawa et al., 1996, Nature, 382:635-8; Su et al., 1999, J Immunol., 162:7128-7132; Zou et al., 1998, Nature, 393:595-9). In addition, manipulation of CXCR-4 alters the homing and retention of progenitors in adult mice further supporting its critical role (Ma et al., 1999, Immunity, 10:463-71; Peled et al., 1999, Science, 283:845-8). Selectins and integrins are also believed to participate in this process and have been identified as mediators of retention or adhesion of primitive cells to bone marrow in vivo or in vitro (Greenberg et al., 2000, Blood, 95:478-86; Naiyer et al., 1999, Blood, 94:4011-9; Rood et al., 1999, Exp. Hematol., 27:1306-14; van der Loo et al., 1998, J. Clin. Invest. 102:1051-61; Williams et al., 1991, Nature, 352:438-41; Zanjani et al., 1999, Blood, 94:2515-22). These studies, however, have not provided a complete understanding of progenitor cell localization.

Understanding exogenous signaling molecules which may contribute to the expansion of the progenitor cell population is important to defining therapeutic procedures.

SUMMARY OF THE INVENTION

The invention relates in some aspects to methods for manipulating stem and progenitor cells. It has been discovered, surprisingly, that activation of the Parathyroid Hormone/Parathyroid Hormone-related Protein (PTH/PTHrP) receptor in cells forming a microenvironment according to the invention leads to an enhancement in the growth (including increase in self-renewal/number increase) and/or maintenance of progenitor and stem cells (e.g., hematopoietic stem cells, hematopoietic progenitor cells, mesenchymal stem cells, epithelial stem cells, neural stem cells).

In one aspect the invention relates to a method for enhancing the growth or maintenance of hematopoietic stem or progenitor cells. The method involves, contacting a cell expressing a PTH/PTHrP receptor with an agent that activates the PTH/PTHrP receptor in an amount effective to support the growth or maintenance of hematopoietic stem or progenitor cells. In important embodiments, the cell expressing a PTH/PTHrP receptor is present in the immediate vicinity of a hematopoietic stem or progenitor cell. In one embodiment, the cell expressing a PTH/PTHrP receptor is a lymphoreticular stromal cell. In a further embodiment, the cell expressing a PTH/PTHrP receptor is a hematopoietic progenitor cell. Contacting of the cell expressing a PTH/PTHrP receptor with an agent that activates the PTH/PTHrP receptor may occur in vitro or in vivo. In important embodiments, the agent that activates the PTH/PTHrP receptor is PTH (including recombinant synthetic human PTH (1-34) and active PTH fragments), a PTH analogue, or a PTH/PTHrP receptor agonist. The growth or maintenance of hematopoietic progenitor cells may occur in vitro or in vivo.

In another aspect of the invention a method for inducing hematopoietic stem or progenitor cell self-renewal, is provided. The method involves co-culturing a hematopoietic stem or progenitor cell with a cell expressing a PTH/PTHrP receptor, and contacting the cell expressing a PTH/PTHrP receptor with an agent that activates the PTH/PTHrP receptor to induce self-renewal of the hematopoietic stem or progenitor cell. The co-culturing may occur in vitro or ex vivo.

In a further aspect of the invention a method for enhancing the growth or maintenance of hematopoietic stem or progenitor cells in a subject, is provided. The method involves administering to a subject in need of such treatment an agent that activates the PTH/PTHrP receptor in cells of the subject expressing the PTH/PTHrP receptor, in an amount effective to support the growth or maintenance of hematopoietic stem or progenitor cells. In some embodiments, the cell expressing a PTH/PTHrP receptor is a lymphoreticular stromal cell. In certain embodiments, the cell expressing a PTH/PTHrP receptor is a hematopoietic stem or progenitor cell. In important embodiments, the agent that activates the PTH/PTHrP receptor is PTH, a PTH analogue, or a PTH/PTHrP receptor agonist. In further important embodiments, the subject in need of such treatment is a bone marrow donor. The bone marrow donor may have donated bone marrow, or has yet to donate bone marrow. In certain embodiments, the subject in need of such treatment is a bone marrow transplant recipient. In one embodiment, the subject in need of such treatment is a subject having hematopoietic progenitor cells under environmental stress. Environmental stresses include increased temperatures (e.g., fever), physical trauma, oxidative, osmotic and chemical stress (e.g. a chemotherapeutic agent), and/or irradiation (e.g. ultra-violet (UV), X-ray, gamma, alpha, or beta irradiation).

In further embodiments the subject in need of such treatment is a subject having immune system deficiencies. Immune system deficiencies include subjects with chronic infections, subjects treated with radiation or chemotherapy, subjects with abnormally low CD4 cell counts, subjects with genetic immune deficiencies. The subject can also be a subject with any one or more categories of hematopoietic cell deficiency such as abnormally low monocytes, macrophages, neutrophils, T-cells, B-cells, erythrocytes, platelets, basophils.

In a further aspect of the invention a method for providing hematopoietic cells to a subject in need thereof, is provided. The method involves administering an agent that activates a PTH/PTHrP receptor in cells of the subject expressing the PTH/PTHrP receptor in an amount effective to increase hematopoietic stem or progenitor cell production. In some embodiments, the cell expressing a PTH/PTHrP receptor is a lymphoreticular stromal cell. In certain embodiments, the cell expressing a PTH/PTHrP receptor is a hematopoietic stem or progenitor cell. In important embodiments, the agent that activates the PTH/PTHrP receptor is PTH, a PTH analogue, or a PTH/PTHrP receptor agonist. In further important embodiments, the subject in need of such treatment has received, will receive or is concurrently receiving chemotherapy or radiation therapy for cancer. The subject can have a disorder including but not limited to myeloma, non-Hodgkin's lymphoma, Hodgkins lyphoma and leukaemia. The subject can have a disorder characterized by a lack of functional blood cells, including but not limited to a platelet deficiency, anemia (e.g., aplastic anemia, sickle cell anemia, fanconi's anemia and acute lymphocytic anemia) and neutropenia. The subject can have a disorder characterized by a lack of functional immune cells, including but not limited to, lymphocytopenia, lymphorrhea, lymphostasis and AIDS. The subject can also be a stem cell donor. In important embodiments, the subject in need of such treatment has received, will receive or is concurrently receiving an immuno-suppressive drug. In further important embodiments, the subject in need of such treatment has received, will receive or is concurrently receiving G-CSF.

According to another aspect of the invention a method for enhancing mobilization of hematopoietic stem or progenitor cells, is provided. The method involves administering to a subject in need of such treatment an agent that activates a PTH/PTHrP receptor in an amount sufficient to enhance mobilization of hematopoietic stem or progenitor cells in the subject. In important embodiments, the subject is a bone marrow donor.

In a further aspect of the invention a method for increasing the ratio of normal to abnormal hematopoietic cells in a subject in need thereof, is provided. The method involves contacting a population of cells expressing a PTH/PTHrP receptor in the subject with an agent that activates the PTH/PTHrP receptor in an amount effective to expand a population of hematopoietic stem or progenitor cells, thereby increasing the ratio of normal to abnormal hematopoietic cells in the subject. In some embodiments, the population of cells expressing a PTH/PTHrP receptor are present in the immediate vicinity of the population of hematopoietic stem or progenitor cells. The population of cells expressing a PTH/PTHrP receptor can be but are not limited to osteoblasts, lymphoreticular stromal cells, and a mixture of osteoblasts and lymphoreticular stromal cells. In important embodiments, the abnormal cells are leukemic cells (e.g., lymphoblastic) or pre-leukemic cells (e.g., myelodysplasic cells). In important embodiments, the agent that activates the PTH/PTHrP receptor is PTH, a PTH analogue, or a PTH/PTHrP receptor agonist. In further important embodiments, the subject in need of such treatment has or is at risk of having leukemia, wherein the leukemia is chronic (e.g., chronic myeloid, chronic myelogenous or chronic granulocytic leukemia) or the leukemia is acute (e.g., acute lymphoblastic leukemia or acute nonlymphoblastic leukemia).

In a further aspect of the invention a method for treating a subject having or at risk of having leukemia, is provided. The method involves administering to the subject a PTH, a PTH analogue, or a PTH/PTHrP receptor agonist in an amount effective to increase the amount of normal hematopoietic stem and progenitor cells; and decreasing the amount of leukemic or pre-leukemic cells, thereby treating a subject having or at risk of having leukemia. In important embodiments, the subject in need of such treatment has or is at risk of having leukemia, wherein the leukemia is chronic (e.g., chronic myeloid, chronic myelogenous or chronic granulocytic leukemia) or the leukemia is acute (e.g., acute lymphoblastic leukemia or acute nonlymphoblastic leukemia).

In a further aspect of the invention a method for decreasing the amount of abnormal hematopoietic cells in a subject in need thereof, is provided. The method involves administering to the subject a PTH, a PTH analogue, or a PTH/PTHrP receptor agonist in an amount effective to increase the amount of normal hematopoietic stem and progenitor cells in the subject, thereby decreasing the amount of abnormal hematopoietic cells in the subject. In important embodiments, the abnormal cells are leukemic cells (e.g., lymphoblastic) or pre-leukemic cells (e.g., myelodysplasic cells). In important embodiments, the agent that activates the PTH/PTHrP receptor is PTH, a PTH analogue, or a PTH/PTHrP receptor agonist. In further important embodiments, the subject in need of such treatment has or is at risk of having leukemia, wherein the leukemia is chronic (e.g., chronic myeloid, chronic myelogenous or chronic granulocytic leukemia) or the leukemia is acute (e.g., acute lymphoblastic leukemia or acute nonlymphoblastic leukemia).

According to a further aspect, the invention provides an isolated population of cells treated with PTH. The population of cells is preferably a stromal cell population. The cells can be ex vivo cells isolated from a subject. Alternatively, the cells can be in vitro cultured cells. In one embodiment, the isolated cells are homogeneous. In an alternative embodiment, the isolated cells are heterogeneous and include two or more cell types. One of the cell types is preferably a stromal cell.

Methods of the invention can be applied to non-hematopoietic stem and progenitor cells.

In another aspect, a method for enhancing the growth or maintenance of mesenchymal stem cells, is provided. The method involves contacting a cell expressing a PTH/PTHrP receptor with an agent that activates the PTH/PTHrP receptor in an amount effective to support the growth or maintenance of mesenchymal stem cells. In important embodiments, the cell expressing a PTH/PTHrP receptor is present in the immediate vicinity of a mesenchymal stem cell. In one embodiment, the cell expressing a PTH/PTHrP receptor is a bone (e.g., osteoblast) breast (e.g., mammary cells), skin (e.g., keratinocytes and fibroblasts), epithelial, lung (e.g., alveolar cells), urogenital, or gastrointestinal cell. The growth or maintenance of mesenchymal stem cells may occur in vitro or in vivo.

In yet another aspect, a method for increasing the ratio of normal to abnormal bone, mammary, skin, lung, urogenital or gastrointestinal cells in a subject in need thereof, is provided. The method involves contacting a population of cells expressing a PTH/PTHrP receptor in the subject with an agent that activates the PTH/PTHrP receptor in an amount effective to expand a population of mesenchymal stem or progenitor cells, thereby increasing the ratio of normal to abnormal bone, mammary, skin, lung, urogenital or gastrointestinal cells in the subject.

In yet another aspect, a method for enhancing the growth or maintenance of epithelial stem cells, is provided. The method involves, contacting a cell expressing a PTH/PTHrP receptor with an agent that activates the PTH/PTHrP receptor in an amount effective to support the growth or maintenance of epithelial stem cells. In important embodiments, the cell expressing a PTH/PTHrP receptor is present in the immediate vicinity of a epithelial stem cell. In one embodiment, the cell expressing a PTH/PTHrP receptor is a breast (e.g., mammary cells), skin (e.g., keratinocytes, fibroblasts, hair follicle cells), epithelial, lung (e.g, alveolar cells) urogenital or gastrointestinal. The growth or maintenance of epithelial stem cells may occur in vitro or in vivo.

In yet another aspect, a method for increasing the ratio of normal to abnormal mammary, skin, lung, urogenital or gastrointestinal cells in a subject in need thereof, is provided. The method involves contacting a population of cells expressing a PTH/PTHrP receptor in the subject with an agent that activates the PTH/PTHrP receptor in an amount effective to expand a population of epithelial stem or progenitor cells, thereby increasing the ratio of normal to abnormal mammary, skin, lung, urogenital or gastrointestinal cells in the subject.

In yet another aspect, a method for enhancing the growth or maintenance of neural stem cells, is provided. The method involves, contacting a cell expressing a PTH/PTHrP receptor with an agent that activates the PTH/PTHrP receptor in an amount effective to support the growth or maintenance of neural stem cells. In important embodiments, the cell expressing a PTH/PTHrP receptor is present in the immediate vicinity of a neural stem cell. In one embodiment, the cell expressing a PTH/PTHrP receptor is a astrocyte, oligodendrocyte, glial cell, GABAergic neuron or dopaminergic neuron. In another embodiment, the cell expressing a PTH/PTHrP receptor is located in a particular anatomical region of the brain, such as a cell of the cerebellum, (e.g., a purkinje cell, a granule cell), telencephalon, diencephalons, mesencephalon, medulla, pons, thalamus, hippocampus, trigeminal ganglion or leptomeninges. The growth or maintenance of neural stem cells may occur in vitro or in vivo.

In yet another aspect, a method for increasing the ratio of normal to abnormal neural cells in a subject in need thereof, is provided. The method involves contacting a population of cells expressing a PTH/PTHrP receptor in the subject with an agent that activates the PTH/PTHrP receptor in an amount effective to expand a population of neural stem or progenitor cells, thereby increasing the ratio of normal to abnormal neural cells in the subject.

In yet another aspect, the present invention provides a kit for enhancing the growth or maintenance of hematopoietic stem or progenitor cells, epithelial stem cells or mesenchymal stem cells and instructions for using an agent that activates the PTH/PTHrP receptor to enhance the growth or maintenance of the cells in accordance with the methods described herein.

In yet another aspect, a method of identifying a cellular product that increases a population of stem or progenitor cells is provided, the method comprising the steps of:
a) contacting a cell expressing a PTH/PTHrP receptor with an agent that activates the PTH/PTHrP receptor;
b) collecting proteins or mRNA encoding proteins produced by the cell expressing a PTH/PTHrP receptor in response to the agent of step a);
c) contacting a stem or progenitor cell with one or more proteins of step b);
d) measuring a physiologic effect exhibited by the stem or progenitor cell; and
e) isolating one or more proteins associated with the physiologic effect, wherein the physiologic effect comprises increased replication of the stem or progenitor cells.

Each of the limitations of the invention can encompass various embodiments of the invention. It is, therefore, anticipated that each of the limitations of the invention involving any one element or combinations of elements can be included in each aspect of the invention.

BRIEF DESCRIPTION OF THE DRAWINGS

FIG. 6. Plot showing percent survival of mock injected and PTH injected mice.

FIGS. 7A-G. Depict the treatment protocol (FIG. 7A) and: analysis of HSC in peripheral blood following chemotherapy, PTH treatment and G-CSF treatment in terms of white blood count (WBC, FIG. 7B), neutrophils count (NE, FIG. 7C), hemoglobin concentration (Hb, FIG. 7D) and platelet count (Plt, FIG. 7E); and analysis of HSC in bone marrow (FIG. 7F) and peripheral blood (FIG. 7G) with G-CSF upon prior and concurrent treatment with PTH.

FIG. 8. Depicts the structure of the amino acid peptide derivative of PTH Leu$^{27}$cyclo[Glu$^{22}$-Lys$^{26}$]-hPTH(1-31)-NH$_2$ (Ostabolin-C™) (SEQ ID NO:1).

FIG. 13. a) Bar graph showing percent annexin-positive cells upon culture with varying doses of recombinant osteopontin. b) Bar graph showing cell number×$10^4$ for leukemia cells under different culture conditions.

DETAILED DESCRIPTION OF THE INVENTION

Figure 1:
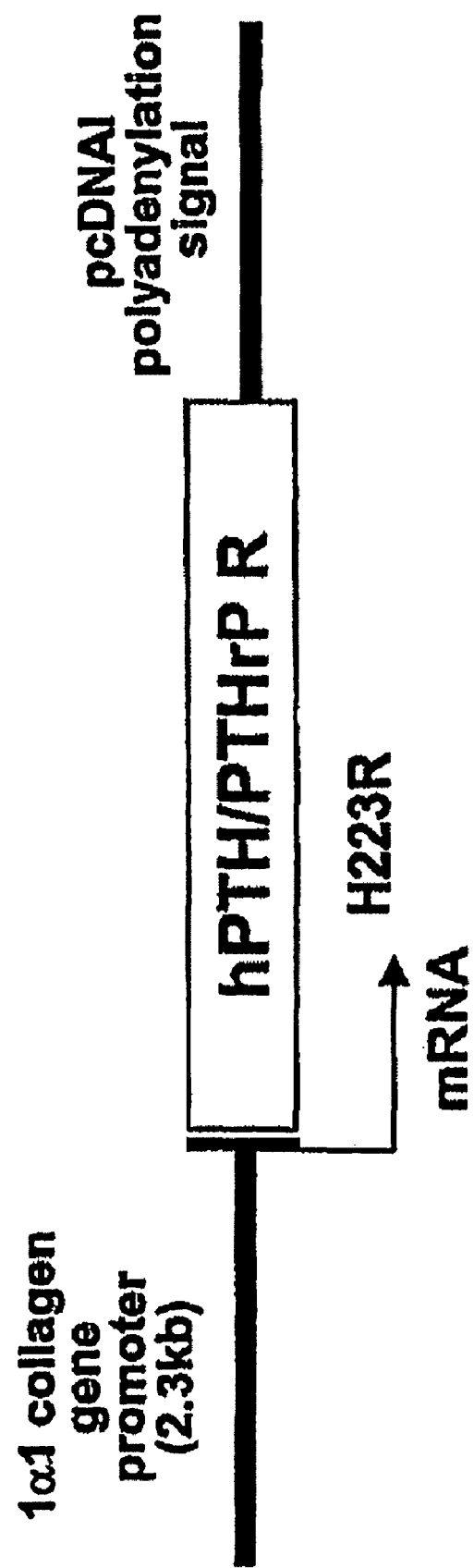
FIG. 1. Figure showing hPTH/PTHrP receptor construct.

New methods for manipulating progenitor and stem cells have been identified according to the invention. These methods and related products have great therapeutic and research value. For instance, hematopoietic progenitor cells are used for transplantation to supplement the immune system of immune deficient patients. These cells have many additional therapeutic uses. Prior to the invention, however, the ability to isolate and purify hematopoietic progenitor cells has been limited. These cells reside in the bone marrow, making their isolation a technically complex procedure. Additionally, there are not many commercially viable methods for identifying these cells in a sample. The invention has solved many of these problems.

According to the invention, a method for enhancing the growth or maintenance of stem or progenitor cells is provided. The method involves, contacting a cell expressing a PTH/PTHrP receptor with an agent that activates the PTH/PTHrP receptor in an amount effective to support the growth or maintenance of stem or progenitor cells (e.g., hematopoietic stem cells, hematopoietic progenitor cells, mesenchymal stem cells, epithelial stem cells, neural stem cells).

As used herein, "enhancing the growth or maintenance" refers to promoting, increasing or enhancing the condition of the stem or progenitor cells, including the survival and differentiation capacity of the cells.

"Stem cells" as used herein refer to immature cells having the capacity to self-renew and to differentiate into the more mature cells (also described herein as "progeny"). Progenitor cells also have the capacity to self-renew and to differentiate into more mature cells, but are committed to a lineage (e.g., hematopoietic progenitors are committed to the blood lineage), whereas stem cells are not necessarily so limited. For the purposes of this disclosure, progenitor cells can be interchangeably described as "stem cells" throughout the specification.

Methods of the invention further provide a means for expansion of non-hematopoietic stem and progenitor cells, such as epithelial, mesenchymal, and neural stem cells. Growth and expansion of such stem cell populations can improve tissue quality among multiple organ systems, including, for example, neural, breast, skin, respiratory, muscle, bone, urogenital or gastrointestinal systems. Furthermore, increasing the amount of epithelial, mesenchymal, or neural stem and progenitor cells in a subject having abnormal cells (e.g., malignant cells) of the same origin can increase the ratio of normal to abnormal cells.

Accordingly, stem cell populations that can benefit from methods of the invention include mesenchymal stem cells. Mesenchymal stem cells are believed to migrate out of the bone marrow, to associate with specific tissues, where they will eventually differentiate into multiple lineages. Enhancing the growth and maintenance of mesenchymal stem cells, in vitro or ex vivo will provide expanded populations that can be used to generate new tissue, including breast, skin, muscle, endothelium, bone, respiratory, urogenital, gastrointestinal connective or fibroblastic tissues.

Mesenchymal stem cells, or "MSCs" are well known in the art. MSCs, originally derived from the embryonal mesoderm and isolated from adult bone marrow, can differentiate to form muscle, bone, cartilage, fat, marrow stroma, and tendon. During embryogenesis, the mesoderm develops into limb-bud mesoderm, tissue that generates bone, cartilage, fat, skeletal muscle and endothelium. Mesoderm also differentiates to visceral mesoderm, which can give rise to cardiac muscle, smooth muscle, or blood islands consisting of endothelium and hematopoietic progenitor cells. Primitive mesodermal or MSCs, therefore, could provide a source for a number of cell and tissue types. A number of MSCs have been isolated. (See, for example, Caplan, A., et al., U.S. Pat. No. 5,486,359; Young, H., et al., U.S. Pat. No. 5,827,735; Caplan, A., et al., U.S. Pat. No. 5,811,094; Bruder, S., et al., U.S. Pat. No. 5,736,396; Caplan, A., et al., U.S. Pat. No. 5,837,539; Masinovsky, B., U.S. Pat. No. 5,837,670; Pittenger, M., U.S. Pat. No. 5,827,740; Jaiswal, N., et al., (1997). *J. Cell Biochem.* 64(2):295-312; Cassiede P., et al., (1996) *J Bone Miner Res.* 9:1264-73; Johnstone, B., et al., (1998) *Exp Cell Res.* 1:265-72; Yoo, et al., (1998) *J Bon Joint Surg Am.* 12:1745-57; Gronthos, S., et al., (1994) *Blood* 84:4164-73; Pittenger, et al., (1999) *Science* 284:143-147). This cell is capable of differentiating into a number of cell types of mesenchymal origin. MSCs can also differentiate into endodermal and ectodermal, including neural, lineages.

Stem cell populations that can benefit from methods of the invention also include epithelial stem cells. The epithelium is the membranous cellular tissue that covers the surface or lines a tube or cavity of an animal body. The epithelium serves to enclose and protect the other parts of the body and may produce secretions and excretions and may be associated with assimilation as seen in the gastrointestinal tract. The epithelium is one of the four primary tissues of the body, which constitutes the epidermis and the lining of respiratory, digestive and genitourinary passages.

Epithelial stem cells are also well-known in the art. Epithelial stem cells are cells that are long-lived, relatively undifferentiated, have a great potential for cell division, and are ultimately responsible for the homeostasis of epithelium. Cells of this type include, but are not limited to, those described in U.S. Pat. Nos. 5,556,783; 5,423,778; Rochat et al., Cell 76:1063 (1994); Jones et al. Cell 73:713 (1993); Jones et al., Cell 80:83 (1995)) and Slack, Science 287:1431-1433 (2000).

Skin is one source of epithelial stem cells. Human skin consists of an outer layer of epithelial cells, the epidermis, and an inner layer of supporting tissue, the dermis. The dermis is a well vascularized tissue that provides support for the epidermis. The dermis contains fibroblasts, which produce various elements of the connective tissue, including the extracellular matrix proteins such as collagens, fibronectin and elastin, which contribute to the strength and flexibility of the skin. The skin also contains various accessory organs such as hair follicles and sweat glands. The epidermis is composed of a continually renewing stratified layer of epithelial cells, called keratinocytes. The basal layer of the epidermis contains epithelial stem cells that divide and give rise to the keratinocytes (among other cell types), which produce keratin as they differentiate and are "pushed" to the surface of the epidermis. Epithelial stem cells ("ESCs") can be obtained from tissues such as the skin and the lining of the gut by known procedures, and can be grown in tissue culture (Rheinwald, 1980, Meth. Cell Bio. 21A:229; Pittelkow and Scott, 1986, Mayo Clinic Proc. 61:771).

Stem cell populations that can benefit from methods of the invention also include neural stem cells. Enhancing the growth and maintenance of neural stem cells, in vitro or ex vivo will provide expanded populations that can be used to generate neural tissue, including astrocytes, oligodendrocytes glial cells, GABAergic and dopaminergic neurons.

Neural stem cells are known in the art (Gage F. H. (2000) *Science* 287:1433:1438; Svendsen C. N. et al, (1999) *Brain Path* 9:499-513; Okabe S. et al. (1996) *Mech Dev* 59:89-102.) It was previously believed that the adult brain no longer contained cells with stem cell potential. However, several studies in rodents, and more recently, non-human primates and humans, have shown that stem cells persist in adult brain. These stem cells can proliferate in vivo and continuously regenerate at least some neuronal cells in vivo. When cultured ex vivo, neural stem cells can be induced to proliferate, as well as to differentiate into different types of neurons and glial cells. When transplanted into the brain, neural stem cells can engraft and generate neural cells and glial cells.

Neural stem cells have been identified in the sub-ventricular zone and the hippocampus of the adult mammalian brain (Ciccolini et al., (1998) J Neuroscience 18: 7869-7880; Palmer et al., (1999) J. Neurosci. 19:8487-97; Reynolds and Weiss, (1992) Science 255:1707-10; Vescovi et al., (1999) Exp Neurol 156:71-83) and can also be present in the ependyma and other presumed non-neurogenic areas of the brain (Doetsch et al., (1999) Cell 97:703-716; Johansson et al., (1999) Cell 96, 25-34; Palmer et al., (1999) J. Neurosci. 19:8487-97). Fetal or adult brain-derived neural stem cells can be expanded ex vivo and induced to differentiate into astrocytes, oligodendrocytes and functional neurons (Ciccolini et al., (1998) J Neuroscience 18: 7869-7880; Johansson et al., (1999) Cell 96, 25-34; Palmer et al., (1999) J. Neurosci. 19:8487-97; Reynolds et al., (1996) Dev Biol 175:1-13; Ryder et al., (1990) J Neurobiol 21: 356-375; Studer et al., (1996) Exp Brain Res 108, 328-36; Vescovi et al., (1993) Neuron 11, 951-66). In vivo, undifferentiated neural stem cells cultured for variable amounts of time eventually differentiate into glial cells, GABAergic and dopaminergic neurons (Flax et al., (1998) Nature Biotechnol 16:1033-1038; Gage et al., (1995) Proc Natl Adad Sci USA 92:11879-83; Suhonen et al., (1996) Nature 383:624-7).

Cells expressing a PTH/PTHrP receptor can be present in the immediate vicinity of neural stem cells. For example, the cell expressing a PTH/PTHrP receptor can be located in a particular anatomical region of the brain, such as a cell of the cerebellum, (e.g., a purkinje cell, a granule cell), telencephalon, diencephalons, mesencephalon, medulla, pons, thalamus, hippocampus, trigeminal ganglion or leptomeninges (Weaver et al. (1995) Mol. Brain. Res. 28:296.

In another aspect, a method for enhancing the growth or maintenance of hematopoietic stem or progenitor cells is provided. The method involves, contacting a cell expressing a PTH/PTHrP receptor with an agent that activates the PTH/PTHrP receptor in an amount effective to support the growth or maintenance of hematopoietic stem or progenitor cells.

It has been discovered according to some aspects of the invention that activation of the parathyroid hormone/parathyroid hormone-related protein receptor (PTH/PTHrP) results in enhancing the growth (including increase in self-renewal/number increase) or maintenance of hematopoietic stem or progenitor cells. This effect is believed to be mediated by cells expressing the receptor that are present in the bone marrow microenvironment. An agent that activates the receptor (such as parathyroid hormone-PTH), may therefore serve as a stimulant to enhance stem or progenitor cell production in vivo and in vitro. This represents an unexpected discovery with important clinical implications for the field of progenitor cell transplantation.

Expanding the number of bone marrow derived progenitor cells is a long-sought solution to the inadequate number of stem and progenitor cells available for transplantation in hematologic and oncologic disease. A beneficial effect can be envisioned in at least the following settings: (i) the enhancement of stem and progenitor cell numbers in vivo; this could be either prior to harvest to facilitate obtaining stem and progenitor cells, or to accelerate stem and progenitor cell recovery following bone marrow transplantation, and/or (ii) ex vivo expansion of harvested stem and progenitor cells. A method to increase stem and progenitor cell numbers in vivo would potentially reduce the time and discomfort associated with bone marrow/peripheral progenitor cell harvesting and increase the pool of progenitor cell donors. Currently approximately 25% of autologous donor transplants are prohibited for lack of sufficient progenitor cells. In addition, less than 25% of patients in need of allogeneic transplant can find a histocompatible donor. Umbilical cord blood banks currently exist and cover the broad racial make-up of the general population, but are currently restricted in use to children due to inadequate progenitor cell numbers in the specimens. A method to increase stem and progenitor cell numbers would permit cord blood to be useful for adult patients, thereby expanding the use of allogeneic transplantation.

It has also been discovered according to some aspects of the invention that enhancing the growth (including increase in self-renewal/number increase) or maintenance of hematopoietic stem or progenitor cells through PTH/PTHrP stimulation will increase the ratio of normal to abnormal hematopoietic cells. A beneficial effect can be envisioned for leukemic and pre-leukemic conditions, where the progressive domination of abnormal cells results in disease.

It is well known in the art that hematopoietic cells include pluripotent stem cells, multipotent progenitor cells (e.g., a lymphoid stem cell), and/or progenitor cells committed to specific hematopoietic lineages. The progenitor cells committed to specific hematopoietic lineages may be of T cell lineage, B cell lineage, dendritic cell lineage, Langerhans cell lineage and/or lymphoid tissue-specific macrophage cell lineage. It is also known in the art that hematopoietic progenitor cells may or may not include $CD34^+$ cells. $CD34^+$ cells are immature cells present in the "blood products" described below, express the CD34 cell surface marker, and are believed to include a subpopulation of cells with the "progenitor cell" properties defined above.

The hematopoietic stem and progenitor cells can be obtained from blood products. A "blood product" as used in the present invention defines a product obtained from the body or an organ of the body containing cells of hematopoietic origin. Such sources include unfractionated bone marrow, umbilical cord, peripheral blood, liver, thymus, lymph and spleen. It will be apparent to those of ordinary skill in the art that all of the aforementioned crude or unfractionated blood products can be enriched for cells having "hematopoietic progenitor cell" characteristics in a number of ways. For example, the blood product can be depleted from the more differentiated progeny. The more mature, differentiated cells can be selected against, via cell surface molecules they express. Additionally, the blood product can be fractionated selecting for $CD34^+$ cells. As mentioned earlier, $CD34^+$ cells are thought in the art to include a subpopulation of cells capable of self-renewal and pluripotentiality. Such selection can be accomplished using, for example, commercially available magnetic anti-CD34 beads (Dynal, Lake Success, N.Y.). Unfractionated blood products can be obtained directly from a donor or retrieved from cryopreservative storage.

Progeny of hematopoietic stem and progenitor cells comprise granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), and monocytes (e.g., monocytes, macrophages).

In important embodiments, the cell expressing a PTH/PTHrP receptor is present in the immediate vicinity of a hematopoietic stem or progenitor cell. In certain embodiments, the cell expressing a PTH/PTHrP receptor is a lymphoreticular stromal cell. "Lymphoreticular stromal cells" as used herein may include, but are not limited to, all cell types present in a lymphoid tissue which are not lymphocytes or lymphocyte precursors or progenitors, e.g., osteoblasts, epithelial cells, endothelial cells, mesothelial cells, dendritic cells, splenocytes and macrophages. Lymphoreticular stromal cells also include cells that would not ordinarily function as lymphoreticular stromal cells, such as fibroblasts, which have been genetically altered to secrete or express on their cell surface the factors necessary for the maintenance, growth and/or differentiation of hematopoietic stem and progenitor cells, including their progeny. Lymphoreticular stromal cells are derived from the disaggregation of a piece of lymphoid tissue (see discussion below). Such cells according to the invention are capable of supporting in vitro the maintenance, growth and/or differentiation of hematopoietic stem and progenitor cells, including their progeny. By "lymphoid tissue" it is meant to include bone marrow, peripheral blood (including mobilized peripheral blood), umbilical cord blood, placental blood, fetal liver, embryonic cells (including embryonic stem cells), aortal-gonadal-mesonephros derived cells, and lymphoid soft tissue. "Lymphoid soft tissue" as used herein includes, but is not limited to, tissues such as thymus, spleen, liver, lymph node, skin, tonsil, adenoids and Peyer's patch, and combinations thereof.

Lymphoreticular stromal cells provide the supporting microenvironment in the intact lymphoid tissue for the maintenance, growth and/or differentiation of hematopoietic progenitor cells, including their progeny. The microenvironment includes soluble and cell surface factors expressed by the various cell types which comprise the lymphoreticular stroma. Generally, the support which the lymphoreticular stromal cells provide may be characterized as both contact-dependent and non-contact-dependent.

Lymphoreticular stromal cells may be autologous ("self") or non-autologous ("non-self," e.g., allogeneic, syngeneic or xenogeneic) with respect to hematopoietic progenitor cells or antigen presenting cells. "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. Lymphoreticular stroma cells may be obtained from the lymphoid tissue of a human or a non-human subject at any time after the organ/tissue has developed to a stage (i.e., the maturation stage) at which it can support the maintenance growth and/or differentiation of hematopoietic stem and progenitor cells. The stage will vary between organs/tissues and between subjects. In primates, for example, the maturation stage of thymic development is achieved during the second trimester. At this stage of development the thymus can produce peptide hormones such as thymulin, $\alpha_1$ and $\beta_4$-thymosin, and thymopoietin, as well as other factors required to provide the proper microenvironment for T cell differentiation. The different maturation stages for the different organs/tissues and between different subjects are well known in the art.

Lymphoreticular stromal cells, preferably express the PTH/PTHrP receptor. The lymphoid tissue from which lymphoreticular stromal cells are derived usually determines the lineage-commitment hematopoietic stem and progenitor cells undertake, resulting in the lineage-specificity of the differentiated progeny. In certain embodiments, the lymphoreticular stromal cells are thymic stromal cells and the multipotent progenitor cells and/or committed progenitor cells are committed to a T cell lineage. In other embodiments, the lymphoreticular stromal cells may be splenic stromal cells and the multipotent progenitor cells and/or committed progenitor cells are committed to a B cell lineage. Also surprising, according to the invention, has been the discovery that the highest yield of differentiated progeny occurs when human hematopoietic progenitor cells are cultured in the presence of xenogeneic (non-human) lymphoreticular stromal cells. Preferably the xenogeneic lymphoreticular stromal cells are of murine origin.

Various other embodiments are provided, wherein the lymphoreticular stromal cells may be genetically altered. In certain embodiments, lymphoreticular stromal cells, preferably express the PTH/PTHrP receptor (endogenously or via genetic alteration). The lymphoreticular stromal cells may be transfected with exogenous DNA that encodes, for example, one of the hematopoietic growth factors described elsewhere herein.

As mentioned earlier, lymphoreticular stromal cells are derived from the disaggregation of a piece of lymphoid tissue, forming cell suspensions. Preferably, single cell suspensions are generated. These lymphoreticular stromal cell suspensions may be used directly, or made non-mitotic by procedures standard in the tissue culture art. Examples of such methods are irradiation of lymphoreticular stromal cells with a gamma-ray source or incubation of the cells with mitomycin C for a sufficient amount of time to render the cells mitotically inactive. Mitotic inactivation is preferred when the lymphoreticular stromal cells are of human origin (to eliminate progenitor cells that may be present in the suspension). The lymphoreticular stromal cells may then be seeded into a three-dimensional matrix of the invention and permitted to attach to a surface of the porous, solid matrix. It should be noted that the lymphoreticular stromal cells may alternatively be cryopreserved for later use or for storage and shipment to remote locations, such as for use in connection with the sale of kits. Cryopreservation of cells cultured in vitro is well established in the art. Subsequent to isolation (and/or mitotic inactivation) of a cell sample, cells may be cryopreserved by first suspending the cells in a cryopreservation medium and then gradually freezing the cell suspension. Frozen cells are typically stored in liquid nitrogen or at an equivalent temperature in a medium containing serum and a cryopreservative such as dimethyl sulfoxide.

The co-culture of hematopoietic stem or progenitor cells (and progeny thereof) with lymphoreticular stromal cells, according to certain aspects of the invention preferably occurs under conditions sufficient to produce a percent increase in the number of lymphoid tissue origin cells deriving from the hematopoietic stem or progenitor cells. The conditions used refer to a combination of conditions known in the art (e.g., temperature, $CO_2$ and $O_2$ content, nutritive media, time-length, etc.). The time sufficient to increase the number of cells is a time that can be easily determined by a person skilled in the art, and can vary depending upon the original number of cells seeded. The amounts of hematopoietic stem or progenitor cells and lymphoreticular stromal cells initially introduced (and subsequently seeded) into the porous solid matrix may vary according to the needs of the experiment. The ideal amounts can be easily determined by a person skilled in the art in accordance with needs. Hematopoietic progenitor cells may be added at different numbers. As an example, discoloration of the media over a certain period of time can be used as an indicator of confluency. Additionally, and more precisely, different numbers of hematopoietic stem and progenitor cells or volumes of the blood product can be cultured under identical conditions, and cells can be harvested and counted over regular time intervals, thus generating the "control curves". These "control curves" can be used to estimate cell numbers in subsequent assays.

The conditions for determining colony forming potential are similarly determined. Colony forming potential is the ability of a cell to form progeny. Assays for this are well known to those of ordinary skill in the art and include seeding cells into a semi-solid matrix, treating them with growth factors, and counting the number of colonies.

In preferred embodiments of the invention, the hematopoietic stem and progenitor cells may be harvested. "Harvesting" hematopoietic progenitor cells is defined as the dislodging or separation of cells from the matrix. This can be accomplished using a number of methods, such as enzymatic, non-enzymatic, centrifugal, electrical, or size-based methods, or preferably, by flushing the cells using media (e.g. media in which the cells are incubated). The cells can be further collected, separated, and further expanded generating even larger populations of differentiated progeny.

As mentioned above, the stem and progenitor cells, and progeny thereof, can be genetically altered. Genetic alteration of a stem and progenitor cell includes all transient and stable changes of the cellular genetic material which are created by the addition of exogenous genetic material. Examples of genetic alterations include any gene therapy procedure, such as introduction of a functional gene to replace a mutated or nonexpressed gene, introduction of a vector that encodes a dominant negative gene product, introduction of a vector engineered to express a ribozyme and introduction of a gene that encodes a therapeutic gene product. Natural genetic changes such as the spontaneous rearrangement of a T cell receptor gene without the introduction of any agents are not included in this embodiment. Exogenous genetic material includes nucleic acids or oligonucleotides, either natural or synthetic, that are introduced into the stem and progenitor cells. The exogenous genetic material may be a copy of that which is naturally present in the cells, or it may not be naturally found in the cells. It typically is at least a portion of a naturally occurring gene which has been placed under operable control of a promoter in a vector construct.

Various techniques may be employed for introducing nucleic acids into cells. Such techniques include transfection of nucleic acid-CaPO$_4$ precipitates, transfection of nucleic acids associated with DEAE, transfection with a retrovirus including the nucleic acid of interest, liposome mediated transfection, and the like. For certain uses, it is preferred to target the nucleic acid to particular cells. In such instances, a vehicle used for delivering a nucleic acid according to the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. For example, where liposomes are employed to deliver the nucleic acids of the invention, proteins which bind to a surface membrane protein associated with endocytosis may be incorporated into the liposome formulation for targeting and/or to facilitate uptake. Such proteins include proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

In the present invention, the preferred method of introducing exogenous genetic material into cells is by transducing the cells in situ on the matrix using replication-deficient retroviruses. Replication-deficient retroviruses are capable of directing synthesis of all virion proteins, but are incapable of making infectious particles. Accordingly, these genetically altered retroviral vectors have general utility for high-efficiency transduction of genes in cultured cells, and specific utility for use in the method of the present invention. Retroviruses have been used extensively for transferring genetic material into cells. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with the viral particles) are provided in the art.

The major advantage of using retroviruses is that the viruses insert efficiently a single copy of the gene encoding the therapeutic agent into the host cell genome, thereby permitting the exogenous genetic material to be passed on to the progeny of the cell when it divides. In addition, gene promoter sequences in the LTR region have been reported to enhance expression of an inserted coding sequence in a variety of cell types. The major disadvantages of using a retrovirus expression vector are (1) insertional mutagenesis, i.e., the insertion of the therapeutic gene into an undesirable position in the target cell genome which, for example, leads to unregulated cell growth and (2) the need for target cell proliferation in order for the therapeutic gene carried by the vector to be integrated into the target genome. Despite these apparent limitations, delivery of a therapeutically effective amount of a therapeutic agent via a retrovirus can be efficacious if the efficiency of transduction is high and/or the number of target cells available for transduction is high.

Yet another viral candidate useful as an expression vector for transformation of cells is the adenovirus, a double-stranded DNA virus. Like the retrovirus, the adenovirus genome is adaptable for use as an expression vector for gene transduction, i.e., by removing the genetic information that controls production of the virus itself. Because the adenovirus functions usually in an extrachromosomal fashion, the recombinant adenovirus does not have the theoretical problem of insertional mutagenesis. On the other hand, adenoviral transformation of a target cell may not result in stable transduction. However, more recently it has been reported that certain adenoviral sequences confer intrachromosomal integration specificity to carrier sequences, and thus result in a stable transduction of the exogenous genetic material.

Thus, as will be apparent to one of ordinary skill in the art, a variety of suitable vectors are available for transferring exogenous genetic material into cells. The selection of an appropriate vector to deliver a therapeutic agent for a particular condition amenable to gene replacement therapy and the optimization of the conditions for insertion of the selected expression vector into the cell, are within the scope of one of ordinary skill in the art without the need for undue experimentation. The promoter characteristically has a specific nucleotide sequence necessary to initiate transcription. Optionally, the exogenous genetic material further includes additional sequences (i.e., enhancers) required to obtain the desired gene transcription activity. For the purpose of this discussion an "enhancer" is simply any nontranslated DNA sequence which works contiguous with the coding sequence (in cis) to change the basal transcription level dictated by the promoter. Preferably, the exogenous genetic material is introduced into the cell genome immediately downstream from the promoter so that the promoter and coding sequence are operatively linked so as to permit transcription of the coding sequence. A preferred retroviral expression vector includes an exogenous promoter element to control transcription of the inserted exogenous gene. Such exogenous promoters include both constitutive and inducible promoters.

Naturally-occurring constitutive promoters control the expression of essential cell functions. As a result, a gene under the control of a constitutive promoter is expressed under all conditions of cell growth. Exemplary constitutive promoters include the promoters for the following genes which encode certain constitutive or "housekeeping" functions: hypoxanthine phosphoribosyl transferase (HPRT), dihydrofolate reductase (DHFR) (Scharfmann et al., 1991, Proc. Natl. Acad. Sci. USA, 88:4626-4630), adenosine deaminase, phosphoglycerol kinase (PGK), pyruvate kinase, phosphoglycerol mutase, the actin promoter (Lai et al., 1989, Proc. Natl. Acad. Sci. USA, 86:10006-10010), and other constitutive promoters known to those of skill in the art. In addition, many viral promoters function constitutively in eukaryotic cells. These include: the early and late promoters of SV40; the long terminal repeats (LTRS) of Moloney Leukemia Virus and other retroviruses; and the thymidine kinase promoter of Herpes Simplex Virus, among many others. Accordingly, any of the above-referenced constitutive promoters can be used to control transcription of a heterologous gene insert.

Genes that are under the control of inducible promoters are expressed only or to a greater degree, in the presence of an inducing agent, (e.g., transcription under control of the metallothionein promoter is greatly increased in presence of certain metal ions). Inducible promoters include responsive elements (REs) which stimulate transcription when their inducing factors are bound. For example, there are REs for serum factors, steroid hormones, retinoic acid and cyclic AMP. Promoters containing a particular RE can be chosen in order to obtain an inducible response and in some cases, the RE itself may be attached to a different promoter, thereby conferring inducibility to the recombinant gene. Thus, by selecting the appropriate promoter (constitutive versus inducible; strong versus weak), it is possible to control both the existence and level of expression of a therapeutic agent in the genetically modified cell. Selection and optimization of these factors for delivery of a therapeutically effective dose of a particular therapeutic agent is deemed to be within the scope of one of ordinary skill in the art without undue experimentation, taking into account the above-disclosed factors and the clinical profile of the patient.

In addition to at least one promoter and at least one heterologous nucleic acid encoding the therapeutic agent, the expression vector preferably includes a selection gene, for example, a neomycin resistance gene, for facilitating selection of cells that have been transfected or transduced with the expression vector. Alternatively, the cells are transfected with two or more expression vectors, at least one vector containing the gene(s) encoding the therapeutic agent(s), the other vector containing a selection gene. The selection of a suitable promoter, enhancer, selection gene and/or signal sequence (described below) is deemed to be within the scope of one of ordinary skill in the art without undue experimentation.

The selection and optimization of a particular expression vector for expressing a specific gene product in an isolated cell is accomplished by obtaining the gene, preferably with one or more appropriate control regions (e.g., promoter, insertion sequence); preparing a vector construct comprising the vector into which is inserted the gene; transfecting or transducing cultured cells in vitro with the vector construct; and determining whether the gene product is present in the cultured cells.

The foregoing (Table 1), represent only examples of genes that can be delivered according to the methods of the invention. Suitable promoters, enhancers, vectors, etc., for such genes are published in the literature associated with the foregoing trials. In general, useful genes replace or supplement function, including genes encoding missing enzymes such as adenosine deaminase (ADA) which has been used in clinical trials to treat ADA deficiency and cofactors such as insulin and coagulation factor VIII. Genes which affect regulation can also be administered, alone or in combination with a gene supplementing or replacing a specific function. For example, a gene encoding a protein which suppresses expression of a particular protein-encoding gene can be administered. The invention is particularly useful in delivering genes which stimulate the immune response, including genes encoding viral antigens, tumor antigens, cytokines (e.g. tumor necrosis factor) and inducers of cytokines (e.g. endotoxin).

Employing the culture conditions described in greater detail below, it is possible according to the invention to preserve hematopoietic stem and progenitor cells and to stimulate the expansion of hematopoietic stem and progenitor cell number and/or colony forming unit potential. Once expanded, the cells, for example, can be returned to the body to supplement, replenish, etc. a patient's hematopoietic stem and progenitor cell population. This might be appropriate, for example, after an individual has undergone chemotherapy. There are certain genetic conditions wherein hematopoietic

TABLE 1

| Human Gene Therapy Protocols Approved by RAC: 1990-1994 | | |
|---|---|---|
| Severe combined immune deficiency (SCID) due to ADA deficiency | Autologous lymphocytes transduced with human ADA gene | Jul. 31, 1990 |
| Advanced cancer | Tumor-infiltrating lymphocytes transduced with tumor necrosis factor gene | Jul. 31, 1990 |
| Advanced cancer | Immunization with autologous cancer cells transduced with tumor necrosis factor gene | Oct. 07, 1991 |
| Advanced cancer | Immunization with autologous cancer cells transduced with interleukin-2 gene | Oct. 07, 1991 |
| Asymptomatic patients infected with HIV-1 | Murine Retro viral vector encoding HIV-1 genes [HIV-IT(V)] | Jun. 07, 1993 |
| AIDS | Effects of a transdominant form of rev gene on AIDS Intervention | Jun. 07, 1993 |
| Advanced cancer | Human multiple-drug resistance (MDR) gene transfer | Jun. 08, 1993 |
| HIV infection | Autologous lymphocytes transduced with catalytic ribozyme that cleaves HIV-1 RNA (Phase I study) | Sep. 10, 1993 |
| Metastatic melanoma | Genetically engineered autologous tumor vaccines producing interleukin-2 | Sep. 10, 1993 |
| HIV infection | Murine Retro viral vector encoding HIV-IT(V) genes (open label Phase I/II trial) | Dec. 03, 1993 |
| HIV infection (identical twins) | Adoptive transfer of syngeneic cytotoxic T lymphocytes (Phase I/II pilot study) | Mar. 03, 1994 |
| Breast cancer (chemo-protection during therapy) | Use of modified Retro virus to introduce chemotherapy resistance sequences into normal hematopoietic cells (pilot study) | Jun. 09, 1994 |
| Fanconi's anemia | Retro viral mediated gene transfer of the Fanconi anemia complementation group C gene to hematopoietic progenitors | Jun. 09, 1994 |
| Metastatic prostate Carcinoma | Autologous human granulocyte macrophage-colony stimulating factor gene transduced prostate cancer vaccine *(first protocol to be approved under the accelerated review process; ORDA = Office of Recombinant DNA Activities) | ORDA/NIH Aug. 03, 1994* |
| Metastatic breast cancer | In vivo infection with breast-targeted Retro viral vector expressing antisense c-fox or antisense c-myc RNA | Sep. 12, 1994 |
| Metastatic breast cancer (refractory or recurrent) | Non-viral system (liposome-based) for delivering human interleukin-2 gene into autologous tumor cells (pilot study) | Sep. 12, 1994 |
| Mild Hunter syndrome | Retro viral-mediated transfer of the iduronate-2-sulfatase gene into lymphocytes | Sep. 13, 1994 |
| Advanced mesothelioma | Use of recombinant adenovirus (Phase I study) | Sep. 13, 1994 | stem and progenitor cell numbers are decreased, and the methods of the invention may be used in these situations as well.

It also is possible to take the increased numbers of hematopoietic stem and progenitor cells produced according to the invention and stimulate them with hematopoietic growth agents that promote hematopoietic cell maintenance, expansion and/or differentiation, and also influence cell localization, to yield the more mature blood cells, in vitro. Such expanded populations of blood cells may be applied in vivo as described above, or may be used experimentally as will be recognized by those of ordinary skill in the art. Such differentiated cells include those described above, as well as T cells, plasma cells, erythrocytes, megakaryocytes, basophils, polymorphonuclear leukocytes, monocytes, macrophages, eosinophils and platelets.

In all of the in vitro and ex vivo culturing methods according to the invention, except as otherwise provided, the media used is that which is conventional for culturing cells. Examples include RPMI, DMEM, Iscove's, etc. Typically these media are supplemented with human or animal plasma or serum. Such plasma or serum can contain small amounts of hematopoietic growth factors. The media used according to the present invention, however, can depart from that used conventionally in the prior art.

The growth agents of particular interest in connection with the present invention are hematopoietic growth factors. By hematopoietic growth factors, it is meant factors that influence the survival, proliferation or differentiation of hematopoietic stem and progenitor cells. Growth agents that affect only survival and proliferation, but are not believed to promote differentiation, include the interleukins 3, 6 and 11, stem cell factor and FLT-3 ligand. Hematopoietic growth factors that promote differentiation include the colony stimulating factors such as GMCSF, GCSF, MCSF, Tpo, Epo, Oncostatin M, and interleukins other than IL-3, 6 and 11. The foregoing factors are well known to those of ordinary skill in the art. Most are commercially available. They can be obtained by purification, by recombinant methodologies or can be derived or synthesized synthetically.

"Stromal cell conditioned medium" refers to medium in which the aforementioned lymphoreticular stromal cells have been incubated. The incubation is performed for a period sufficient to allow the stromal cells to secrete factors into the medium. Such "stromal cell conditioned medium" can then be used to supplement the culture of hematopoietic stem and progenitor cells promoting their proliferation and/or differentiation.

Thus, when cells are cultured without any of the foregoing agents, it is meant herein that the cells are cultured without the addition of such agent except as may be present in serum, ordinary nutritive media or within the blood product isolate, unfractionated or fractionated, which contains the hematopoietic stem and progenitor cells.

One method for modulating hematopoietic cell function according to the invention is a method for enhancing mobilization of hematopoietic progenitor cells by using agents that activate the PTH/PTHrP receptor. Current practice during bone marrow transplantation involves the isolation of bone marrow cells from the bone marrow and/or peripheral blood of donor subjects. About one third of these subjects do not "yield" enough hematopoietic progenitor cells from their bone marrow and/or peripheral blood so that their marrow can be considered suitable for transplantation. Using the methods of the invention, the "yield" may be enhanced. For example, agents that activate the PTH/PTHrP receptor could result in "mobilization" of hematopoietic progenitor cells and the efficiency of hematopoietic progenitor cell isolation from subjects treated with such agents may be improved (especially from the subject's peripheral blood). This then results in an increase in the number of donor samples that may be used in transplantation.

Thus, in some aspects a method for enhancing mobilization of hematopoietic cells in a subject is provided. The method involves administering to a subject an agent that activates the PTH/PTHrP receptor to enhance mobilization of hematopoietic progenitor cells in the subject.

As used herein, a subject is a human, non-human primate, cow, horse, pig, sheep, goat, dog, cat or rodent. Human hematopoietic progenitor cells and human subjects are particularly important embodiments.

As used herein a "an agent that activates the PTH/PTHrP receptor" is a compound that includes Parathyroid hormone (PTH), parathyroid related-protein (PTHrP), and analogues thereof.

The term "obtaining" as in "obtaining the agent that activates the PTH/PTHrP receptor" is intended to include purchasing, synthesizing or otherwise acquiring the agent (or indicated substance or material).

The normal function of PTH is to maintain extracellular fluid calcium concentration. PTH acts directly on bone and kidney and indirectly on the intestines. PTH production in healthy individuals is closely regulated by the concentration of serum ionized calcium. Tendencies towards hypocalcemia, for example, induced by a calcium-deficient diet, are balanced by an increased PTH secretion. The increase in PTH levels increases the rate of bone resorption, thereby increasing the calcium flow from bone into blood, reduces the renal clearance of calcium, and increases the efficiency of calcium absorption in the intestines.

The physiological role of the parathyroid hormone-related protein (PTHrP) is not fully understood, but is thought to be acting principally as a paracrine or autocrine factor. PTHrP plays a role in fetal development as well as in adult physiology. PTHrP is produced by many cell types, including brain, pancreas, heart, lung, memory tissue, placenta, endothelial, and smooth muscle cells. In adults, PTHrP is thought to have little to do with calcium homeostasis, except in disease states.

PTH and PTHrP are distinct proteins and products of different genes. However, they share a similar bioactivity profile and a very limited sequence homology, indicating that they may have evolved from a common ancestral gene. Eight out of the 13 first amino acid residues at the N-terminus are identical. Both PTH, an 84 amino acid residues peptide, and PTHrP, a 139 to 173 amino acid residues peptide, bind to the PTH receptor (often referred to as the PTH/PTHrP receptor) and stimulate the same intracellular signaling pathways.

Parathyroid hormone (PTH) is an 84 amino acid polypeptide which is normally secreted from the parathyroid glands. PTH has an important physiological role to maintain serum calcium within a narrow range. Furthermore, it has anabolic properties when given intermittently. This has been well documented in a number of animal and open clinical studies, recently reviewed by Dempster, D. W. et al. (Endocrine Reviews 1993, vol. 14, 690-709). PTH has a multitude of effects on bone. Part of it is through the remodeling cycle. PTH causes both increased activation frequency and a positive balance per cycle. Human PTH may be obtained through peptide synthesis or from genetically engineered yeast, bacterial or mammalian cell hosts. Synthetic human PTH is commercially available from Bachem Inc., Bubendorf, Switzerland. Production of recombinant human parathyroid hormone is disclosed in e.g. EP-B-0383751.

The mature circulating form of parathyroid hormone is comprised of 84 amino acid residues. For most bone-related activities the truncated form of PTH, PTH(1-34), is a full agonist like the native 84 amino-acid hormone. Amino-terminal truncation results in polypeptides that are competitive antagonists of PTH-stimulated adenylate cyclase. For example, [Tyr$^{34}$]bPTH(7-34)NH$_2$ retains moderate affinity for renal PTH receptors, but does not have any agonist activity; weak receptor binding activity is retained in a fragment as small as PTH(25-34) (M. Rosenblatt, et al., 1980, Endocrinol., 107:545-550). In contrast, carboxyl-terminal truncations of PTH(1-34) produce agonists with progressively lower affinities. PTH(1-25) is inactive, however, it is possible to construct mutants of PTH(1-25) that will have activity (Shimizu et al. J. Biol. Chem. 276:52 (2001)). The principal receptor-binding domain of PTH is reported to include amino acid residues 25-34 and the principal activation domain is reported to include amino acid residues 1-6.

The term "parathyroid hormone" (PTH) encompasses naturally occurring human PTH, as well as synthetic or recombinant PTH (rPTH). Further, the term "parathyroid hormone" encompasses full-length PTH(1-84) as well as PTH fragments. It will thus be understood that fragments of PTH variants, in amounts giving equivalent biological activity to PTH(1-84), can be incorporated in the formulations according to the invention, if desired. In this context, the term "biologically active" should be understood as eliciting a sufficient response in a bioassay for PTH activity according to the methods described herein. Fragments of PTH incorporate at least the amino acid residues of PTH necessary for a biological activity similar to that of intact PTH. Examples of such fragments are PTH(1-31), PTH(1-34), PTH(1-36), PTH(1-37), PTH(1-38), PTH(1-41), PTH(28-48), PTH(1-25) variants and PTH(25-39).

The term "parathyroid hormone" also encompasses variants and functional analogs of PTH. The present invention thus includes pharmaceutical formulations comprising such PTH variants and functional analogues, carrying modifications like substitutions, deletions, insertions, inversions or cyclisations, but nevertheless having substantially the biological activities of parathyroid hormone. Stability-enhanced variants of PTH are known in the art from e.g. WO 92/11286 and WO 93/20203. Variants of PTH can e.g. incorporate amino acid substitutions that improve PTH stability and half-life, such as the replacement of methionine residues at positions 8 and/or 18, and replacement of asparagine at position 16.

Biologically active PTH/PTHrP analogs of any mammalian species, e.g., human, bovine, porcine, or rabbit, can be used in the methods of the present inventions, with human analogues being preferred. Suitable PTH/PTHrP analogs for use in accordance with the present invention include those described in U.S. Pat. Nos. 5,589,452, 5,849,695, 5,695,955, 6,362,163, 6,147,186 and 6,583,114. Cyclized PTH analogs are disclosed in e.g. WO 98/05683.

U.S. Pat. Nos. 5,589,452, 5,695,955, and 6,583,114 describe synthetic PTH analogs of PTH and PTHrP in which certain amino acid residues (22-31) form an amphipathic alpha helix.

U.S. Pat. No. 5,849,695 describes PTH analogs of PTH and PTHrP in which the serine amino acid at position 3, the glutamine amino acid at position 6, the histidine amino acid at position 9 or combinations thereof are substituted by other natural or synthetic amino acids.

U.S. Pat. Nos. 6,362,163 and 6,147,186 describe PTHrP analogs that have been converted into PTH-2 receptor agonists by the substitution of one or more amino acid residues of PTHrP to the corresponding residue(s) of PTH (e.g., the amino acid sequence is altered at amino acid residues 5 and 23, for example, (Ile$_5$, Trp$_{23}$) PTHrP-(1-36) wherein the alteration at PTHrP amino acid residue 5 is an amino acid substitution of histidine for isoleucine, and the alteration at PTHrP amino acid residue 23 is an amino acid substitution of phenylalanine for tryptophan).

Various PTH/PTHrP products, including fragments, variants and analogues, are already commercially available, or in various stages of development. For example, synthetic bovine PTH(1-34) is available from Bachem, Inc., Torrance, Calif.; synthetic human PTHrP(1-34) amide is available from Merck Sharp and Dohme, West Point, Pa.; BIM-44058, a PTH (1-34) analog, is manufactured by Ipsen Ltd, Slough, Berkshire, U.K.; the PTH analogue Ostabolin-C™ is manufactured by Zelos Therapeutics Inc., Ottawa, ON, Canada; and the recombinant PTH analogue Forteo™ is manufactured by Eli Lilly and Company, Indianapolis, Ind.

The Ostabolin-C™ peptide is a 31 amino acid peptide derivative of PTH. The Ostabolin-C™ peptide differs from PTH in that the peptide has been cyclized by a lactam moiety between Glu$^{22}$ and Lys$^{26}$ and replacement of Lys$^{27}$ with Leu. The Ostabolin-C™ peptide can be represented by Leu$^{27}$cyclo [Glu$^{22}$-Lys$^{26}$]-hPTH(1-31)-NH$_2$ as shown in FIG. 8 (SEQ ID NO: 1).

Cyclized PTH analogues are also described in U.S. Pat. Nos. 5,556,940; 5,955,425; 6,110,892; 6,316,410; and 6,541,450 the teachings of all of which are hereby incorporated by reference in their entirety.

Under some circumstances, PTH is a bone anabolic agent, and promotes bone formation. However, PTH can stimulate bone resorption as well. It has been reported that high-dose, continuous administration of PTH results in a lowered bone mass but low-dose, intermittent administration of PTH can increase bone mass. PTH administered continuously reportedly causes an increase in the number of bone cells, including osteoclasts, and an increase in bone remodeling. These increases reportedly are apparent within hours after PTH administration and persist for hours after PTH is withdrawn. PTH administration intermittently over days in humans and animals reportedly leads to a net stimulation of bone formation. For example, see Neer et al., 2001, N. Engl. J. Med., 344:1434-1441. In contrast, continuous exposure to elevated levels of PTH leads to osteoclast-mediated bone resorption. Several groups have investigated the use of PTH and PTHrP analogues as agents to treat osteoporosis. These efforts are described in U.S. Pat. Nos. 5,747,456; 5,849,695; 4,656,250; 6,051,686; and 6,316,410.

In one embodiment the subject is a bone marrow donor. By enhancing mobilization of bone marrow cells, the need for bone marrow isolation may be obviated. As a result of this mobilization, bone marrow cells leave the bone marrow and enter the blood circulation of the subject undergoing treatment. The circulating bone marrow cells can then be easily isolated using the techniques of the invention or other methods know in the art. For instance, these methods may reduce the need for large bone marrow donations for therapeutic procedures. The methods enable the isolation of hematopoietic stem and progenitor cells from peripheral blood by encouraging localization from the bone marrow to the blood and thus, eliminating the need for bone marrow donation.

One of skill in the art would be aware of methods for isolating hematopoietic stem and progenitor cells from peripheral blood. For example blood in PBS is loaded into a tube of Ficoll (Ficoll-Paque, Amersham) and centrifuged at 1500 rpm for 25-30 minutes. After centrifugation the white center ring is collected as containing hematopoietic stem cells.

Hematopoietic stem and progenitor cell manipulation is also useful as a supplemental treatment to chemotherapy, e.g., hematopoietic progenitor cells may be caused to localize into the peripheral blood and then isolated from a subject that will undergo chemotherapy, and after the therapy the cells can be returned (e.g. ex vivo therapy may also be performed on the isolated cells). Thus, the subject in some embodiments is a subject undergoing or expecting to undergo an immune cell depleting treatment such as chemotherapy. Most chemotherapy agents used act by killing all cells going through cell division. Bone marrow is one of the most prolific tissues in the body and is therefore often the organ that is initially damaged by chemotherapy drugs. The result is that blood cell production is rapidly destroyed during chemotherapy treatment, and chemotherapy must be terminated to allow the hematopoietic system to replenish the blood cell supplies before a patient is re-treated with chemotherapy. This can be avoided using the methods of the invention.

Once the hematopoietic stem and progenitor cells are mobilized from the bone marrow to the peripheral blood, a blood sample can be isolated in order to obtain the hematopoietic progenitor cells. These cells can be transplanted immediately or they can be processed in vitro first. For instance, the cells can be expanded in vitro and/or they can be subjected to an isolation or enrichment procedure. It will be apparent to those of ordinary skill in the art that the crude or unfractionated blood products can be enriched for cells having "hematopoietic progenitor cell" characteristics. Some of the ways to enrich include, e.g., depleting the blood product from the more differentiated progeny. The more mature, differentiated cells can be selected against, via cell surface molecules they express. Additionally, the blood product can be fractionated selecting for $CD34^+$ cells. Such selection can be accomplished using, for example, commercially available magnetic anti-CD34 beads (Dynal, Lake Success, N.Y.). In preferred embodiments, however, the methods of the invention may be used to isolate the hematopoietic stem and progenitor cells.

Methods for isolation of hematopoietic stem and progenitor cells are well-known in the art, and typically involve purification techniques based on cell surface markers and functional characteristics. The hematopoietic stem and progenitor cells can be isolated from bone marrow, blood, cord blood, fetal liver and yolk sac, and give rise to multiple hematopoietic lineages and can reinitiate hematopoiesis for the life of a recipient. (See Fei, R., et al., U.S. Pat. No. 5,635,387; McGlave, et al., U.S. Pat. No. 5,460,964; Simmons, P., et al., U.S. Pat. No. 5,677,136; Tsukamoto, et al., U.S. Pat. No. 5,750,397; Schwartz, et al., U.S. Pat. No. 5,759,793; DiGuisto, et al., U.S. Pat. No. 5,681,599; Tsukamoto, et al., U.S. Pat. No. 5,716,827; Hill, B., et al. 1996.) When transplanted into lethally irradiated animals or humans, hematopoietic stem cells can repopulate the erythroid, neutrophil-macrophage, megakaryocyte and lymphoid hematopoietic cell pool. In vitro, hematopoietic stem cells can be induced to undergo at least some self-renewing cell divisions or can be induced to differentiate to the same lineages observed in vivo. Accordingly, methods of the invention can involve the in vitro expansion of hematopoietic stem and progenitor cells by way of co-culture with stimulated PTH/PTHrP receptor expressing cells, thereby recapitulating the in vivo microenvironment.

Hematopoietic stems for use with co-culture-based methods of the invention can be obtained from pluripotent stem cell sources as well. For example, U.S. Pat. No. 5,914,268 describes a pluripotent cell population for use in the development into hematopoietic cells, progenitors and progeny thereof. The pluripotent cell population is derived by culturing an embryonic stem cell population to obtain an embryoid body cell population, which is then followed by culturing said embryoid body cell population under conditions effective to produce said pluripotent cell population. The culturing conditions comprise an embryonic blast cell medium.

The invention further provides methods of immunizing against and/or treating a disorder or disease, such as for example an infectious disease, in an individual. The methods generally involve administering to a subject the compounds of the invention in an amount effective to stimulate hematopoiesis.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

The methods of the invention can be used to treat any disease or disorder in which it is desirable to increase the production of hematopoietic stem and progenitor cells, support the maintenance or survival of hematopoietic stem and progenitor cells, or mobilize hematopoietic stem cells. For example, the methods of the invention can be used to treat patients requiring a bone marrow transplant or a hematopoietic stem or progenitor cell transplant, such as cancer patients undergoing chemo and/or radiation therapy. Methods of the present invention are particularly useful in the treatment of patients undergoing chemotherapy or radiation therapy for cancer, including patients suffering from myeloma, non-Hodgkin's lymphoma, Hodgkins lyphoma, or leukaemia.

Treatment can be used as a means to increase the amount of hematopoietic stem and progenitor cells in disorders where the progressive domination of abnormal hematopoietic cells results in disease, such as in disorders of chronic leukemia (e.g., chronic myeloid, chronic myelogenous or chronic granulocytic leukemia), acute leukemia (e.g., acute lymphoblastic leukemia or acute nonlymphoblastic leukemia) and pre-leukemia (e.g., myelodysplasia). Abnormal cells that can be effectively reduced or eradicated include leukemic cells, such as lymphoblastic leukemic cells. Treatment enables an increase in the ratio of normal to abnormal hematopoietic cells, thereby changing the phenotype of the malignancy such that it is ameliorated or eradicated.

Treatment can further be used as a means to increase the amount of mature cells derived from hematopoietic stem cells (e.g., erythrocytes). For example, disorders or diseases characterized by a lack of blood cells, or a defect in blood cells, can be treated by increasing the production of hematopoietic stem cells. Such conditions include thrombocytopenia (platelet deficiency), and anemias such as aplastic anemia, sickle cell anemia, fanconi's anemia, and acute lymphocytic anemia.

Disorders treated by methods of the invention can be the result of an undesired side effect or complication of another primary treatment, such as radiation therapy, chemotherapy, or treatment with a bone marrow suppressive drug, such as zidovadine, chloramphenical or gangciclovir. Such disorders include neutropenias, anemias, thrombocytopenia, and immune dysfunction. In addition, methods of the invention can be used to treat damage to the bone marrow caused by unintentional exposure to toxic agents or radiation.

The disorder to be treated can also be the result of an infection (e.g., viral infection, bacterial infection or fungal infection) causing damage to stem or progenitor cells.

Immunodeficiencies, such as T and/or B lymphocytes deficiencies, or other immune disorders, such as rheumatoid arthritis and lupus, can also be treated according to the methods of the invention. Such immunodeficiencies may also be the result of an infection (for example infection with HIV leading to AIDS), or exposure to radiation, chemotherapy or toxins.

In addition to the above, further conditions which can benefit from treatment using methods of the invention include, but are not limited to, lymphocytopenia, lymphorrhea, lymphostasis, erythrocytopenia, erthrodegenerative disorders, erythroblastopenia, leukoerythroblastosis; erythroclasis, thalassemia, myelofibrosis, thrombocytopenia, disseminated intravascular coagulation (DIC), immune (autoimmune) thrombocytopenic purpura (ITP), HIV induced ITP, myelodysplasia; thrombocytotic disease, thrombocytosis, congenital neutropenias (such as Kostmann's syndrome and Schwachman-Diamond syndrome), neoplastic associated neutropenias, childhood and adult cyclic neutropaenia; post-infective neutropaenia; myelo-dysplastic syndrome; and neutropaenia associated with chemotherapy and radiotherapy.

Also benefiting from treatment according to methods of the invention are individuals who are healthy, but who are at risk of being affected by any of the diseases or disorders described herein ("at-risk" individuals). At-risk individuals include, but are not limited to, individuals who have a greater likelihood than the general population of becoming cytopenic or immune deficient. Individuals at risk for becoming immune deficient include, but are not limited to, individuals at risk for HIV infection due to sexual activity with HIV-infected individuals; intravenous drug users; individuals who may have been exposed to HIV-infected blood, blood products, or other HIV-contaminated body fluids; babies who are being nursed by HIV-infected mothers; individuals who were previously treated for cancer, e.g., by chemotherapy or radiotherapy, and who are being monitored for recurrence of the cancer for which they were previously treated; and individuals who have undergone bone marrow transplantation or any other organ transplantation, or patients anticipated to undergo chemotherapy or radiation therapy or be a donor of stem cells for transplantation.

A reduced level of immune function compared to a normal subject can result from a variety of disorders, diseases infections or conditions, including immunosuppressed conditions due to leukemia, renal failure; autoimmune disorders, including, but not limited to, systemic lupus erythematosus, rheumatoid arthritis, auto-immune thyroiditis, scleroderma, inflammatory bowel disease; various cancers and tumors; viral infections, including, but not limited to, human immunodeficiency virus (HIV); bacterial infections; and parasitic infections.

A reduced level of immune function compared to a normal subject can also result from an immundeficiency disease or disorder of genetic origin, or due to aging. Examples of these are immunodeficiency diseases associated with aging and those of genetic origin, including, but not limited to, hyperimmunoglobulin M syndrome, CD40 ligand deficiency, IL-2 receptor deficiency, γ-chain deficiency, common variable immunodeficiency, Chediak-Higashi syndrome, and Wiskott-Aldrich syndrome.

A reduced level of immune function compared to a normal subject can also result from treatment with specific pharmacological agents, including, but not limited to chemotherapeutic agents to treat cancer; certain immunotherapeutic agents; radiation therapy; immunosuppressive agents used in conjunction with bone marrow transplantation; and immunosuppressive agents used in conjunction with organ transplantation.

An "immune system deficiency" shall mean a disease or disorder in which it would be useful to boost a subject's immune response for example to eliminate a tumor or cancer (e.g., tumors of the brain, lung (e.g., small cell and non-small cells), ovary, breast, prostate, colon, as well as other carcinomas and sarcomas) or an infection in a subject.

The compounds of the invention may be administered to the subject alone or in combination with an antigen, such as a tumor antigen, a viral, bacterial, or fungal antigen or other therapeutic.

Examples of infectious virus include: Retroviridae (e.g., human immunodeficiency viruses, such as HIV-1, also referred to as HTLV-III, LAV or HTLV-III/LAV, or HIV-III; and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever virus); Reoviridae (e.g., reoviruses, orbiviruses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herperviridae (herpes simplex virus (HSV) 1 and 2, varicella zoster virus, cytomegalovirus (CMV), herpes viruses); Poxyiridae (variola virsues, vaccinia viruses, pox viruses); and Iridoviridae (e.g., African swine fever virus); and unclassified viruses (e.g., the etiological agents of Spongiform encephalopathies, the agent of delta hepatitides (thought to be a defective satellite of hepatitis B virus), the agents of non-A, non-B hepatitis (class 1—internally transmitted; class 2—parenterally transmitted (i.e., Hepatitis C); Norwalk and related viruses, and astroviruses).

Examples of infectious bacteria include: *Helicobacter pyloris, Borelia burgdorferi, Legionella pneumophilia*, Mycobacteria sps (e.g., *M. tuberculosis, M. avium, M. Intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter erogenes, Klebsiella pneuomiae, Pasturella multicoda, Bacteroides* sp., *Fusobacterium*

*nucleatum, Sreptobacillus moniliformis, Treponema pallidium, Treponema pertenue, Leptospira*, and *Actinomeyces israelli*.

Examples of infectious fungi include: *Cryptococcus neoformans, Histoplasma capsulatum, Coccidioides immitis, Blastomyces dermatitidis, Chlamydia trachomatis, Candida albicans*. Other infectious organisms (i.e., protists) include: *Plasmodium falciparum* and *Toxoplasma gondii*.

When the cells or any compounds of the invention (referred to as therapeutic compositions), such as PTH are administered to a subject, the therapeutic compositions may be administered in pharmaceutically acceptable preparations. Such preparations may routinely contain pharmaceutically acceptable concentrations of salt, buffering agents, preservatives, compatible carriers, and optionally other therapeutic agents.

The therapeutic composition may be administered by any conventional route, including injection or by gradual infusion over time. The administration may, depending on the composition being administered, for example, be oral, pulmonary, intravenous, intraperitoneal, intramuscular, intracavity, subcutaneous, nasal or transdermal. Techniques for preparing aerosol delivery systems containing active agents are well known to those of skill in the art. Generally, such systems should utilize components which will not significantly impair the biological properties of the active agents (see, for example, Sciarra and Cutie, "Aerosols," in *Remington's Pharmaceutical Sciences*, 18th edition, 1990, pp 1694-1712; incorporated by reference). Those of skill in the art can readily determine the various parameters and conditions for producing aerosols without resort to undue experimentation. When using antisense preparations, intravenous or oral administration are preferred. The compositions are administered in effective amounts. An "effective amount" is that amount of a composition that alone, or together with further doses, produces the desired response, e.g. results in an increase in hematopoietic progenitor cells in the bone marrow. The term "therapeutic composition" is used synonymously with the terms "active compound", "active agent" or "active composition" and as used herein refers to any of the active compounds of the invention which produce a biological effect, e.g., PTH, PTH analogues such as those disclosed in U.S. Pat. Nos. 4,086,196, 6,541,450, and WO93/06845, incorporated herein by reference, enriched hematopoietic stem cell preparations, etc. In the case of treating a particular disease or condition characterized by immune deficiency, the desired response is any improvement in immune system function. This may involve only an increase in the actual numbers of hematopoietic stem cells, slowing of onset or progression of an infectious disease arising from the immune system dysfunction, temporarily, although more preferably, it involves an actual improvement in the prevention of disease permanently. This can be monitored by routine methods.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The pharmaceutical compositions used in the foregoing methods preferably are sterile and contain an effective amount of therapeutic composition for producing the desired response in a unit of weight or volume suitable for administration to a patient. The response can, for example, be measured by determining the effect on cell mobilization following administration of the therapeutic composition via a reporter system, or by isolating cells and measuring mobility in vitro. Other assays will be known to one of ordinary skill in the art and can be employed for measuring the level of the response.

When administered, pharmaceutical preparations of the invention are applied in pharmaceutically acceptable amounts and in pharmaceutically acceptable compositions. Such preparations may routinely contain salts, buffering agents, preservatives, compatible carriers, and optionally other therapeutic ingredients. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulfuric, nitric, phosphoric, maleic, acetic, salicylic, p-toluenesulfonic, tartaric, citric, methanesulfonic, formic, succinic, naphthalene-2-sulfonic, pamoic, 3-hydroxy-2-naphthalenecarboxylic, and benzene sulfonic. Also, pharmaceutically acceptable salts can be prepared as alkaline metal or alkaline earth salts, such as sodium, ammonium, magnesium, potassium or calcium salts of the carboxylic acid group.

Suitable buffering agents include: acetic acid and salts thereof (1-2% W/V); citric acid and salts thereof (1-3% W/V); boric acid and salts thereof (0.5-2.5% W/V); and phosphoric acid and salts thereof (0.8-2% W/V).

Suitable preservatives include benzalkonium chloride (0.003-0.03% W/V); chlorobutanol (0.3-0.9% W/V); parabens (0.01-0.25% W/V) and thimerosal (0.004-0.02% W/V).

A variety of administration routes are available. The particular mode selected will depend, of course, upon the particular combination of therapeutic agents selected, the severity of the condition or disorder being treated, or prevented, the condition of the patient, and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, topical, transdermal, sublingual or intramuscular, infusion, parenteral, intravenous, intramuscular, intracavity, as a feed additive, as an aerosol, buccal, aural (e.g., via eardrops), intranasal, inhalation, or subcutaneous. Direct injection could also be preferred for local delivery to the site of injury.

Doses of PTH and/or PTHrP administered can be between about 5 to about 100 micrograms, between about 5 to about 150 micrograms, at least about 5 micrograms, at least about 10 micrograms, at least about 20 micrograms, at least about 25 micrograms, at least about 40 micrograms, at least about 50 micrograms, at least about 60 micrograms, at least about 75 micrograms, at least about 100 micrograms and at least about 150 micrograms per dose.

Although at present subcutaneous administration is routinely employed in the administration of PTH and/or PTHrP, oral administration may be preferred for treatment because of the convenience of the subject (patient) as well as the dosing schedule. Generally, daily oral doses of active compounds will be from about 0.1 microgram per day to 1000 micrograms per day. It is expected that oral doses in the range of 0.5 to 500 micrograms, in one or several administrations per day, will yield the desired results.

Where PTH (1-34) is to be administered it is preferred that a single daily dose in the range of about 10 to about 250 micrograms per day is administered. Even more preferably, a single daily dose in the range about 40 to about 100 micrograms per day is administered. More preferably still, a single daily dose of about 100 micrograms should be administered. Where PTH (1-84) is to be administered it is preferred that a single daily dose in the range of about 10 to about 250 micrograms per day is administered. Even more preferably, a single daily dose in the range about 120 to about 170 micrograms per day is administered. More preferably still, a single daily dose of around about 120 micrograms should be administered.

The exact dosages used may be adjusted appropriately to achieve desired drug levels, local or systemic, depending upon the particular properties of the PTH molecule administered, including its molecular weight and stability, and the mode of administration. For example, it is expected that intravenous administration would be from an order to several orders of magnitude lower dose per day compared to the oral doses. In the event that the response in a subject is insufficient at such doses, even higher doses (or effective higher doses by a different, more localized delivery route) may be employed to the extent that patient tolerance permits.

Preferably the polypeptides of the invention are administered intermittently, which is known in the art to promote anabolic efficacy of PTH, PTHrP and its analogues. Preferred intermittent administration schedules include daily, every second day, every third day, twice per week, every fourth day, every fifth day, every sixth day, and once per week.

The compositions may conveniently be presented in unit dosage form and may be prepared by any of the methods well known in the art of pharmacy. All methods include the step of bringing the compounds of the invention into association with a carrier which constitutes one or more accessory ingredients. In general, the compositions are prepared by uniformly and intimately bringing the compounds of the invention into association with a liquid carrier, a finely divided solid carrier, or both, and then, if necessary, shaping the product.

Compositions suitable for parenteral administration conveniently comprise a sterile aqueous preparation of the compounds of the invention. This preparation is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable dilutant or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono or di-glycerides. In addition, fatty acids such as oleic acid find use in the preparation of injectables. Carrier formulations suitable for oral, subcutaneous, intravenous, intramuscular, etc. are well known in the art.

Compositions suitable for oral administration may be presented as discrete units such as capsules, cachets, tablets, syrups, elixirs or lozenges, each containing a predetermined amount of the compounds of the invention. Compositions suitable for any pulmonary delivery typically are formulated and/or are contained in a nebulizer.

Other delivery systems can include time-release, delayed release or sustained release delivery systems. Such systems can avoid repeated administrations of the compounds of the invention, increasing convenience to the subject and the physician, yet are constructed to provide the anabolic benefit of the polypeptides of the invention. Many types of release delivery systems are available and known to those of ordinary skill in the art. They include polymer based systems such as polylactic and polyglycolic acid, polyanhydrides and polycaprolactone, nonpolymer systems that are lipids including sterols such as cholesterol, liposomes; phoshpholipids; hydrogel release systems; silastic systems; peptide based system; implants and the like. Specific examples include, but are not limited to: (a) erosional systems in which the polypeptide is contained in a form within a matrix, found in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based delivery systems can be used, some of which are adapted for implantation.

Use of a long-term sustained release implant may be particularly suitable for treatment of chronic conditions.

"Long-term" release, as used herein, means that the implant is constructed and arranged to deliver therapeutic levels of the active ingredient for at least 7 days, preferably for 30-60 days and more preferably for longer periods of time (e.g., 12 months or longer). The implant may be positioned at a site of injury, but need not be. Long-term sustained release implants are well-known to those of ordinary skill in the art and include some of the release systems described above. One such implant system is described in U.S. Pat. No. 6,159,490.

Other protocols for the administration of therapeutic compositions will be known to one of ordinary skill in the art, in which the dose amount, schedule of injections, sites of injections, mode of administration and the like vary from the foregoing. Administration of therapeutic compositions to mammals other than humans, e.g. for testing purposes or veterinary therapeutic purposes, is carried out under substantially the same conditions as described above.

Methods of the invention further provide a means for identifying cellular products responsible for mediating the effect of a PTH/PTHrP receptor expressing cell on a stem or progenitor cell. Such cellular products can include, for example, secreted proteins, cell-surface proteins, glycoproteins, lipids or steroids.

Cellular products responsible for mediating the effect of a PTH/PTHrP receptor expressing cell on a stem or progenitor cell may regulate growth, for example, by increasing cell division or "replication." Accordingly, a method of identifying a cellular product that increases a population of stem or progenitor cells is provided, the method comprising the steps of:
- a) contacting a cell expressing a PTH/PTHrP receptor with an agent that activates the PTH/PTHrP receptor;
- b) collecting proteins or mRNA encoding proteins produced by the cell expressing a PTH/PTHrP receptor in response to the agent of step a);
- c) contacting a stem or progenitor cell with one or more proteins of step b);
- d) measuring a physiologic effect exhibited by the stem or progenitor cell; and
- e) isolating one or more proteins associated with the physiologic effect, wherein the physiologic effect comprises increased replication of the stem or progenitor cells.

Methods of isolating individual proteins from samples containing multiple proteins are well known in the art. For example, fractions that test positive for a given physiologic effect (e.g., cell replication) can be further subdivided and re-tested until a sufficiently small population exists. This can be accomplished by obtaining cDNA libraries from activated PTH/PTHrP receptor expressing cells, dividing the libraries into fractions and transfecting pools of cells that are ultimately each co-cultured with the stem or progenitor cells and assayed for a positive response. Positive responses can be matched with one or more cell pools. cDNAs associated with a positive pool can be collected, further subdivided and re-tested until a sufficiently small number of candidate cDNAs are obtained and sequenced.

Other methods of characterizing protein profiles of cells of interest are known in the art, such as Matrix-Assisted Laser-Desorption/Ionization Time-of-Flight Mass Spectrometry ("MALDI-TOF"). The presence and molecular mass of proteins in samples can be determined using MALDI-TOF. Essentially, samples are mixed with a UV-absorbing chemical, crystallized and placed on a steel surface. Laser treatment is used to vaporize and ionize the samples. Peptide ions are then accelerated in an electric filed, and flight times are converted to mass values. A specialized form of MALDI-TOF, known as Surface Enhanced Laser-Desorption/Ionization Time-of-Flight Mass Spectrometry ("SELDI-TOF") expands the approach to include the use of surface is derivatized with polypeptide binding ligands.

Characterization of gene expression profiles in response to PTH/PTHrP receptor activation can also be used to select candidate cDNAs for further testing. For example, increases in gene expression following PTH/PTHrP receptor activation can be detected by methods of subtraction hybridization. cDNAs of interest can then be cloned and expressed in cells that are ultimately co-cultured with the stem or progenitor cells and assayed for a positive response. A sufficiently small number of candidate cDNAs can then be obtained and sequenced.

The following description of experiments performed is exemplary and non-limiting to the scope of the claimed invention.

EXAMPLES

Hematopoietic stem cell frequency is affected by cell autonomous, intrinsic and cell non-autonomous, extrinsic factors. The intrinsic factors have been mapped to specific regions of the mouse genome (de Haan & van Zant, 1997, J. Exp. Med., 186:529-536) that modulate the frequency of hematopoietic stem or restricted progenitor cells, but not both (Morrison et al, 2002, J. Immunol., 168:635-642). Cell cycle dependent kinase inhibitors (CDKIs) that are differentiation stage specific molecular mediators of the hematopoietic stem cell (p21) or progenitor cell (p27) pool size have been identified (Cheng et al., 2000, Nature Med., 6:1235-1240; Cheng et al., 2000, Science, 287:1804-1808). However, the extent to which CDKI expression is affected by cell extrinsic cues provided by microenvironmental stimuli remains ill defined. Overcoming CDKI imposed blockade on cell cycle entry in progenitor cells is readily accomplished ex vivo by a number a cytokines produced by multiple cell types in the bone marrow and with measurable levels in serum. In contrast, adult bone marrow derived hematopoietic stem cells are generally difficult to expand ex vivo and few manipulations have resulted in defined stem cell expansion in vivo. Among these are activation of the cell surface Notch1 and Wnt (Reya et al., 2003, Nature, 423:409-414; Murdoch et al., 2003, Proc. Natl. Acad. Sci. USA, 100:3422-3427) receptors (Stier et al., 2002, Blood, 99:2369-2378) and overexpression of the anti-apoptotic protein, bcl-2 (Weissman I et al., 2000, J. Exp. Med., 191:253-264) or the homeobox protein, HoxB4 (Humphries et al., 1999, Blood, 94:2605-2612). Whether these molecules are altered in physiologic contexts however, has not been defined and what cell types within the hematopoietic microenvironment participate in altering stem cell numbers in vivo have not been previously characterized. The data presented here demonstrate that osteoblast specific expression of an activated receptor can meaningfully affect both the bone and the bone marrow microenvironments changing bone mass and hematopoietic stem cell pool size. The data presented here indicate that osteoblastic cells are regulatory components of the hematopoietic stem cell niche in the mouse. Perturbation in the number and possibly function of these cells by PPR activation can lead to increased stem cell numbers, apparently by increased self-renewal. Physical interaction of the primitive hematopoietic cells with the niche is required and the Notch signaling pathway is involved. These results define the osteoblast as a regulator of hematopoiesis and support an important in vivo interplay between bone and bone marrow.

There are several mechanisms by which PPR activation could influence hematopoiesis. Given the association of hematopoietic stem cells with endosteal surfaces in the paratrabecular space, activated PPR induced changes in the architecture of the bone marrow due to increased bone formation, could affect the surface area for support of stem cells. Through the expansion in physical niches capable of maintaining stem cells, a proportionate increase in the number of stem cells could result. Disaggregated col1-caPPR marrow stroma would not be expected to provide a similar increase in such physical niches, however, and yet is able to increase stem cell support ex vivo. The ability of PTH to increase LTC-IC ex vivo further argues against this explanation as it is similarly unlikely that three dimensional niche construction is induced in the two dimensional monolayer culture of stroma used for that assay. An alternative and more likely explanation is the ability of PPR stimulation to induce osteoblast activation thereby indirectly stimulating hematopoiesis.

To what advantage are bone forming elements coupled to hematopoiesis? In a developmental context, mineralization of the bone and increase in bone mass occur during the second trimester when arguably the developmental imperative is to prepare the host for post-uterine life. Within hematopoietic tissue, this involves a shift from predominantly erythrocyte and platelet production to generation of cellular elements of the innate and adaptive immune system. Hematopoietic cell production transitions from the fetal liver as that organ acquires hepatocyte populations and function. Movement of hematopoiesis to the bone marrow and thymus occur in relative tandem, marking changes in the lineage differentiation profiles of blood elements. With the shifting emphasis on mature cell populations, primitive cell lineage outcomes are modulated and stem cell cycling transitions from robust proliferation in the fetal liver to a less vigorous cycling status in the bone marrow. Stem cells eventually acquire the relative quiescence necessary for long-term maintenance of the mature animal (Cheng et al., 2000, Science, 287:1804-1808). The translocation to bone marrow is accompanied by a transition in stem cell cycling and differentiation. The concurrence of these events with building the skeleton may crudely be viewed as pre-natal necessities for encountering the outside world and as roughly needing proportionate scaling with body mass. Failure to achieve bone marrow hematopoiesis due to either aberrant translocalization or osteopetrosis is accompanied by severe hematopoietic defects including in lineages not thought to be directly affected by the inducing molecular defect (Ma Q et al., 1998, Proc. Natl. Acad. Sci. USA, 95:9448-9453; Dai X M et al., 2002, Blood, 99:111-120). The link of hematopoiesis to bone marrow appears to be important for normal blood homeostasis.

As hematopoiesis expands its cell repertoire, it produces populations of cells capable of feeding back on stem cell function, modifying it in response to stress. To the extent that the osteoblast represents a mature descendent of bone marrow tissue, it also falls into a paradigm set by other mature bone marrow derived cellular elements. Monocyte/macrophages and T cells are well known to have among their products of activation, cytokines that positively and negatively affect hematopoiesis. PTHrP is increased in response to endotoxic stress in animal models (Funk J L et al., 1997, Endocrinology, 138:2665) and activation of osteoblasts can be increased by PTHr stimulation under conditions of stress (Ryder K D et al., 2000, Calcif. Tissu. Int., 67:241-246). Therefore, osteoblasts may be among bone marrow derived cells capable of providing a regulating effect on hematopoiesis in the varying postnatal environment and of providing that modulation in the immediate microenvironment of the stem cell. The osteoblast may be a mesenchymal stem cell product that can be considered a cell with pleiotropic action including feedback regulation of the cells from which it emerges.

As well as acting as a chemotactic stimulus, SDF-1α has been shown to increase hematopoietic stem/progenitor cell number and function through inhibition of apoptotic pathways and promoting the cells to cycle (Lataillade et al., 2000, Blood, 95:756-768; Lataillade et al., 2002, Blood, 99:1117-1129). Hematopoietic cells which have been engineered to overexpress the SDF-1α protein demonstrate increases in number in the adult mouse (Onai et al., 2000, Blood, 96:2074-2080).

Hematopoietic stem cells undergo a development stage-specific translocation during ontogeny and ultimately reside in the adult bone marrow. Maintenance of this highly regenerative cell pool through adult life is dependent upon the relative quiescence of stem cells. The following examples demonstrate new methods for manipulating hematopoietic stem cells for improved therapeutic purposes. The studies focused on whether PTH actions on osteoblastic cells could alter their ability to support hematopoiesis. Hematopoiesis was characterized in a previously described transgenic mouse model in which a constitutively active PPR is expressed in cells of the osteoblastic lineage (Calvi et al., 2001, J. Clin. Invest., 107:277-286).

Example 1

Materials and Methods

Identification of Transgenic Mice. Mice expressing a constitutively active PPR under the control of the 2.3 kb fragment of the mouse al (I) collagen promoter (Rossert et al., 1995, J. Cell. Biol., 129:1421-1432) were previously generated (Calvi et al, 2001, J. Clin. Invest., 107:277-286). The transgene construct (FIG. 1a) contained the 2.3 kb fragment of the mouse α1(I) collagen promoter, 1,880 by encoding the human mutant PPR HKrk-H223R (Calvi et al., 2001, J. Clin. Invest., 107:277-286), and 750 by from the pcDNAI vector (which provides a splice sequence and the consensus polyadenylation signal absent in the cDNA encoding HKrk-H223R). Genotypying and determination of number of insertion sites of the transgene were performed as described (Calvi et al., 2001, J. Clin. Invest., 107:277-286). All studies performed were approved by the institutional animal care committee.

Transgene expression. To confirm transgene expression by in situ hybridization, a 596 by probe (DT7) was generated by PCR amplification of pcDNAI vector sequence in the transgene construct using the reverse primer A1 (5'-TAATAC-GACTCACTATAGGGCGATAAACAAGT-TAACAACAACAAT-3' SEQ ID NO:2) and the forward primer S2 (5'-CTTTGTGAAGGAACCTTACT-3' SEQ ID NO:3) (Calvi et al., 2001, J. Clin. Invest., 107:277-286). The A1 reverse primer sequence includes also the T7 RNA polymerase binding site. The PCR conditions were as follows: 94° C. for 1 min, 58° C. for 45 sec, 72° C. for 1 min, and an additional 10 min at 72° C. at the end of the 45 cycles. In situ hybridizations were performed as described (Calvi et al., 2001, J. Clin. Invest., 107:277-286) using a complementary $^{35}$S-labeled riboprobe transcribed from the DT7 PCR product in order to detect expression of the transgene mRNA in stromal cells.

Sample preparation and histologic analysis. For histologic analysis, transgenic mice and sex-matched wild type littermates were sacrificed by cervical dislocation at 12 weeks of age. Tissues from transgenic and wild type littermates were fixed and stored as described (Calvi et al., 2001, J. Clin. Invest., 107:277-286). Hind limbs were decalcified (Calvi et al., 2001, J. Clin. Invest., 107:277-286), and paraffin blocks were prepared by standard histological procedures.

For immunohistochemistry, decalcified sections from wild-type and transgenic mice were stained with the anti-IL-6 gAb M-19 (1:100 dilution), the anti-SCF gAb G-19 (1:100 dilution), the anti-SDF-1 gAb C-19 (1:50 dilution), the anti-Osteopontin gAb P-18 (1:200 dilution), and the anti-Jagged1 rAb H-114 (1:100 dilution) (Santa Cruz Biotechnology, Inc., Santa Cruz, Calif.). The immunohistochemical staining was performed using a biotinylated rabbit anti goat or goat anti rabbit secondary Ab (Vector Labs, Burlingame, Calif.), Horseradish Peroxidase-Conjugated Streptavidin (Jackson Immuno Research, West Grove, Pa.), and AEC Chromogen (Biocare Medical, Walnut Creek, Calif.), or the Vector ABC Alkaline Phosphatase Kit (Vector Labs, Burlingame, Calif.). Slides were counterstained with Mayer's hematoxylin.

Cytologic analysis. For cytologic analysis, hind limbs were dissected from euthanized wild type and transgenic littermates and cells preparations were obtained by flushing the long bones with α-MEM with 10% fetal calf serum (Gibco) and 1% penicillin/streptomycin. Cells were then cultured in tissue culture flasks at an initial concentration of $5 \times 10^6$ cells/ml. Medium was changed every three days for two weeks or until stromal layers became confluent. Adherent cells were then trypsinized and plated at a concentration of $10^5$ cells/ml in multiwell chambers for 7, 14, 28 days and medium was changed every 3 days. For in situ hybridization, cells were rinsed with PBS three times and then fixed for 1 hr at room temperature with 3.7% PBS buffered formaldehyde. For immunohistochemistry, cells were rinsed with TBS.Ca (1 mM $CaCl_2$, 50 mM Tris/HCl pH 7.4, 150 mM NaCl) four times and fixed for 1 minute with a 1:1 solution of acetone and methanol at room temperature.

Immunocytochemistry. Immunocytochemical staining was performed on Acetone:methanol fixed stromal cells. Cells grown in multiwell plates were incubated with anti-SDF-1 goat polyclonal Ab (Santa Cruz Biotechnology, Santa Cruz, Calif.), 1:50 dilution, for 60 minutes at room temperature, and for 45 minutes with a fluorescein-conjugated secondary antibody. Cells were counterstained with Evan's blue.

Coverslips were mounted with Vectashield containing DAPI (Vector Laboratories, Burlingame, Calif.), and slides were examined using a fluorescent microscope with the appropriate filter.

Preparation of bone marrow stromal layers. Mice were euthanized by $CO_2$ asphyxiation, following which the femurs and tibias were removed and flushed with long-term culture medium (α-MEM with 12.5% horse serum, 12.5% fetal bovine serum, 0.2 mM i-Inositol, 20 μM folic acid, $10^{-4}$ M 2-mercaptoethanol, 2 mM L-glutamine and $10^{-6}$ M hydrocortisone; M5300 Stem Cell Technologies). Mononuclear cells were then cultured in tissue culture flasks at an initial concentration of $5\times10^6$ cells/ml. Medium was changed every three days for two weeks or until stromal layers became confluent.

Flow cytometric analysis. Bone marrow mononuclear cells were isolated as described above. Single cell suspensions were then stained with biotinylated lineage antibodies (CD3, CD4, CD8, Ter119, Gr-1, Mac-1 and B220) and phycoerythrin conjugated anti-Sca-1 and anti-c-Kit (Pharmingen, San Diego, Calif.). Cells were then labeled with a secondary fluorescein isothiocyanante conjugated streptavidin and analyzed on a FACScalibur cytometer (Becton Dickinson and Co., Franklin Lakes, N.J.) using Cell Quest software. To assess cell cycle in the primitive population, bone-marrow mononuclear cells (BM MNCs) were stained with lineage antibodies, anti-Sca-1, PyroninY (RNA dye) and Hoechst 33342 (DNA dye) as described (Cheng et al., 2000, Nature Med., 6:1235-1240). For intracellular NICD staining, lin$^-$Sca-1$^+$c-Kit$^+$ cells were permeabilized using the Fix and Perm Cell Permeabilization Kit (Caltag) according to manufacturer's instructions and incubated with 1 μg of anti-NICD antibody. A secondary goat-anti mouse antibody was then used to detect the anti-NICD.

Colony forming unit assay. Mononuclear cells were isolated from the bone marrow and cultured at $10^4$ cells/ml in the following medium: 0.9% methylcellulose, 15% FBS, 1% BSA, 10 μg/ml rh insulin, 200 μg/ml human transferrin, $10^{-4}$ M 2-mercaptoethanol, 2 mM L-glutamine, 50 ng/ml rmSCF, 10 ng/ml rmIL-3, 10 ng/ml rhIL-6 and 3 units/ml rhEpo (M3434; Stem Cell Technologies, Vancouver, Canada). At day 10, the total number of colonies were counted and reported as total CFU-Cs.

Long-term culture initiating cell assay. Murine bone marrow stromal cells from confluent cultures were irradiated (15 Gy) and plated at a concentration of 20,000 cells/well in 96-well plates in long-term culture medium. Cells were then seeded into the plates in two-fold serial limiting dilutions and cultured at 33° C./5% $CO_2$ in a humidified atmosphere. Cultures were maintained for 5 weeks, changing half of the medium in the wells weekly. Following this, the medium was replaced with methylcellulose containing medium supplemented with recombinant cytokines as described above, then scored for colony growth ten days following the addition of the medium.

In vitro treatment with PTH. LTC-IC assays were performed using wild-type stroma and hematopoietic cells. Rat PTH (1-34) (Bachem, Torrance, Calif.) or vehicle was added to each media change either during stroma establishment and/or during culture maintenance to a final concentration of $10^{-7}$ M. Medium was changed every three days for two weeks or until stromal layers became confluent. For alkaline phosphatase staining, primary mononuclear cells obtained as described above from wild-type and or transgenic littermates were then cultured in 24-well plates at an initial concentration of $5\times10^6$ cells/ml. At 10 or 14 days after seeding, medium was suctioned off, and the adherent cells were gently rinsed twice in PBS. After fixation in 10% Neutral Formalin Buffer for 30 minutes at room temperature, alkaline phosphatase activity was determined histochemically by incubation for 45 minutes at RT with a mixture of 0.1 mg/ml naphthol AS-MX phosphate (Sigma), 0.5% N,N-dimethylformamide, 0.6 mg/ml red violet LB salt (Sigma) in 0.1 M Tris-HCl (pH 8.5). Alkaline phosphatase positive cells were counted at day 10 of culture, when the cultures were subconfluent and individual cells could be identified. For inhibition of γ-secretase activity, 30 μM of γ-secretase inhibitor II (Calbiochem) dissolved in DMSO was added to the long-term culture medium and LTC-IC assays were performed as described. For non-contact LTC-ICs, bone marrow stromal cell layers were plated into 96-well plates as described. Tissue culture inserts with a 0.2 μm pore size membrane (Nunc, Naperville, Ill.) were placed in the wells and bone marrow cells were seeded into the culture inserts.

In vivo PTH administration. For PTH administration, 6-8 week old wild type C57/B male mice were used. Rat PTH (1-34) (80 μg/Kg of body weight) was injected intraperitoneally 5x/week for 4 weeks (n=5). Control mice (n=4) were injected with an equivalent volume of vehicle. At the end of the treatment period, ionized serum calcium was measured by the Ciba/Corning 634 $Ca^{++}$/pH analyzer, and, after euthanasia, the hind limbs and forelimbs were dissected and utilized for cytologic and histologic analysis.

SDF-1 ELISA. The amount of SDF-1 released in the cell culture supernatant was estimated by ELISA. SDF-1 concentration was measured in conditioned media from subconfluent primary stromal cells cultures from transgenic and wild type littermates using the Quantikine SDF-1 Immunoassay (R&D Systems, Inc, Minneapolis, Minn.).

Bone Marrow Transplantation. For the competitive transplant studies, $4\times10^5$ BM MNCs, obtained from CD45.1$^+$ B6.SJL (Jackson Laboratories, Bar Harbor, Me.) mice were mixed with $2\times10^5$ cells from mock injected or PTH injected CD45.2$^+$ C57B1/6 mice. Recipient B6.SJL mice that had been lethally irradiated 24 hours previously with 10 Gy of radiation ($^{137}$Cs source) were injected with cells. After 6 weeks, the mice were euthanized with $CO_2$, the BM was removed and flushed with fully supplemented Iscove's Medium. The relative contribution of engraftment from the different cell sources was assessed by flow cytometry utilizing anti-CD45.1 and anti-CD45.2 antibodies (Pharmingen, San Diego, Calif.). To assess the effects of PTH administration post transplantation, recipient C57B1/6 mice were lethally irradiated and then injected with $2\times10^5$ BM MNCs from a donor B6.SJL mouse. Twenty-four hours following the injection of the cells, mice were injected with PTH or mock injected as described above for four weeks.

Statistical analysis. Results are expressed as mean+/−s.e.m. Data were analyzed using the unpaired two-tailed Student's t test as appropriate for the data set. P<0.05 was considered significant.

Example 2

Transgenic Mouse Experiments

Transgenic mice expressing a constitutively active PPR in cells of the osteoblastic lineage have bone marrow fibrosis and anemia. At 2 and 12 weeks of age, the long bones of the col1-mutPPR mice were characterized by abundant trabeculae and marrow fibrosis. At 12 weeks of age, the long bones of the col1-caPPR mice were histologically examined and demonstrated abundant trabeculae with reduced volume of the marrow space in the metaphyseal area. Given the modest contribution of the metaphyseal area to the total marrow space of the long bones, the magnitude of the reduction in the total bone marrow space in the long bones of the adult transgenic mice was minimal. There was an expansion of the trabecular osteoblastic population as defined by staining with osteocalcin, alkaline phosphatase, collagen type I, osteopontin and MMP-13 (Calvi et al., 2001, J. Clin. Invest., 107:277-286). Hematopoietic cells were found in small regions between trabeculae and few adipocytes were seen. Transgenic mice had mild anemia (hematocrit, wild-type, n=5: 41+/−0.2%; transgenic, n=4: 35.9+/−0.6%, P<0.005), a finding also noted in humans with severe primary hyperparathyroidism (Kotzmann et al., 1997, Horm. Metab. Res., 29:387-392; Sikole, 2000, Med. Hypoteses, 54:236-238). This particular phenotype suggests that constitutive activation of the PPR in cells of the osteoblast lineage may alter normal hematopoiesis by affecting the stromal cell population. Bone marrow stromal cells from transgenic mice express the mRNA of the human mutant PPR in culture.

Figure 2A:
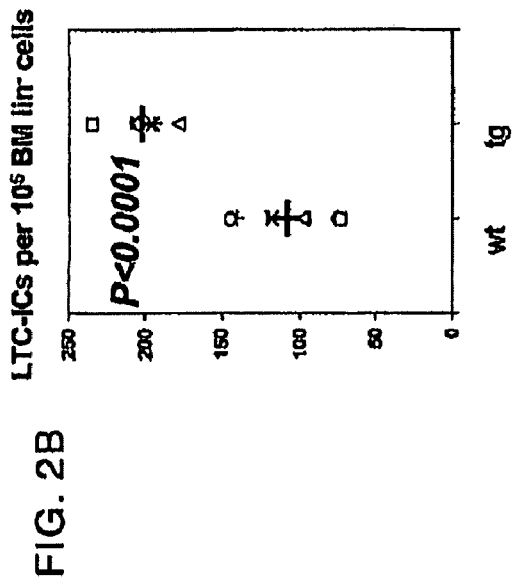
FIG. 2. a) Graph showing the frequency of Sca-1$^+$lin$^-$ subpopulation cells from total bone marrow mononuclear cells. b) Graph showing hematopoietic stem cell frequency of lin$^-$ fraction of bone marrow mononuclear cells. c) Plot showing proportion of Sca-1$^+$lin$^-$ cells in $G_0$ vs $G_1$ phase. d) Graph showing frequency of hematopoietic stem cells using the CFU-C assay.
Figure 2B:
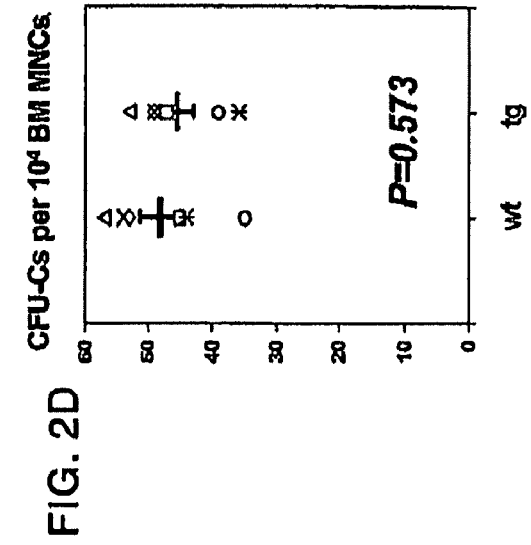
Figure 2C:
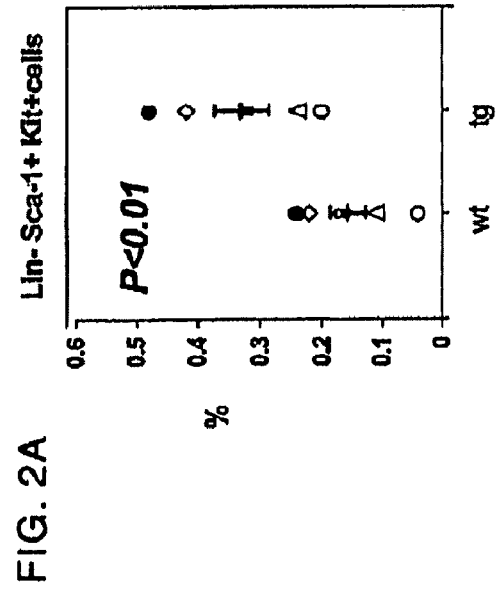
Figure 2D:
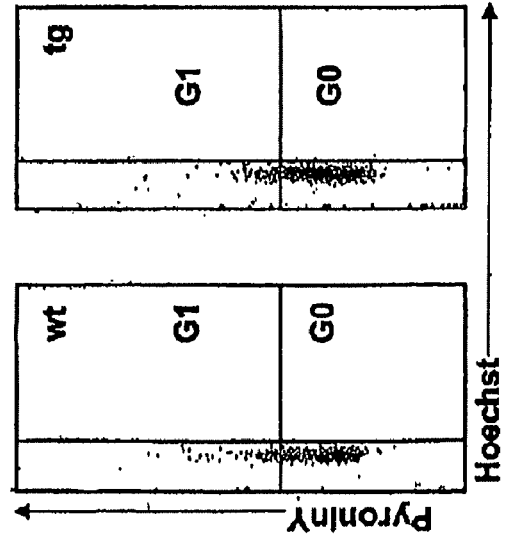

Transgenic mice have an increased number of hematopoietic stem cells in the bone marrow. To elucidate the impact of enhanced activity and number of osteoblasts on hematopoietic stem cells in the transgenic mice, the frequency of hematopoietic stem cells in the bone marrow was first examined by flow cytometry. Analysis of the frequency of the Sca-1$^+$lin$^-$ subpopulation of cells from the total bone marrow mononuclear cells demonstrated that the transgenic mice had a significant increase in the number of candidate stem cells (P=<0.01, FIG. 2a). This proportionate increase had a correspondent increase in the absolute number (mean absolute number per hind limb, wild-type: 32,500+/−8,000 versus transgenic: 65,700+/−7,500). To determine if this corresponded to a functional phenotype, a quantitative, limiting dilution long-term culture initiating-cell (LTC-IC) assay was used that linearly correlates with in vivo hematopoietic stem cell (HSC) function (Ploemacher et al., 1991, Blood, 78:2527-2533). The hematopoietic stem cell frequency was examined using the functional measurement of LTC-IC frequency in the lin$^-$ fraction of bone marrow mononuclear cells. This confirmed an increase of approximately equivalent magnitude in the frequency of LTC-ICs in the transgenic animals (P=<0.0001, FIG. 2b). The magnitude of increase was comparable to the increase seen in immunophenotypically defined primitive cells. As this increase in stem cell frequency could have arisen from an alteration in the cell cycle profile in the transgenic animals, the proportions of Sca-1$^+$lin$^-$ cells which were in the $G_0$ versus $G_1$ phase were analyzed next. No differences were observed between the transgenic and wild-type mice (P=0.768, FIG. 2c). Similarly, measurement of the frequency of hematopoietic progenitor cells using the CFU-C assay demonstrated no difference between the transgenic and wild-type animals (P=0.573; FIG. 2d). These data demonstrate the specificity of the expansion to be at the hematopoietic stem cell level. In particular these data demonstrate that cell expansion was not global across differentiated subsets, but was notably restricted to primitive cells.

Figure 3A:
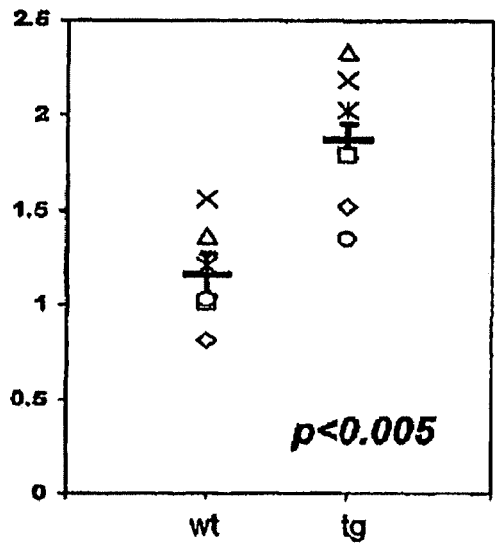
FIG. 3. a) Graph showing support of stromal cells from transgenic mice. b) Plot showing the level of NICD in lin$^-$Sca-1$^+$c-Kit$^+$ hematopoietic stem cells.

PTH action on stromal cells through the PPR is sufficient to increase numbers of hematopoietic stem cells in vitro. As the transgenic mice had an increased frequency of hematopoietic stem cells, the mechanism for this enhancement was investigated. Evaluating the ability of bone marrow stromal cells to support LTC-ICs, it was found that stromal cells derived from the transgenic mice demonstrated enhanced LTC-IC support compared with stromal cells from wild-type animals (P=<0.005, FIG. 3a). Therefore the increased number of primitive cells in the coil-caPPR mice was stroma-determined and was independent of the hematopoietic cell genotype. Due to the transgenic mice having a constitutively active PTH/PTHrP receptor, it was then determined whether or not the addition of exogenous PTH could mimic the previous observations. In these experiments, the stromal cell population was expanded in the presence of PTH, or the LTC-IC assay was performed with PTH in the long-term medium. It was found that the presence of PTH during the expansion of the stromal population from the bone marrow enhanced the ability of the stroma to support LTC-ICs.

Example 3

Transgenic Cell Experiments

Figure 4:
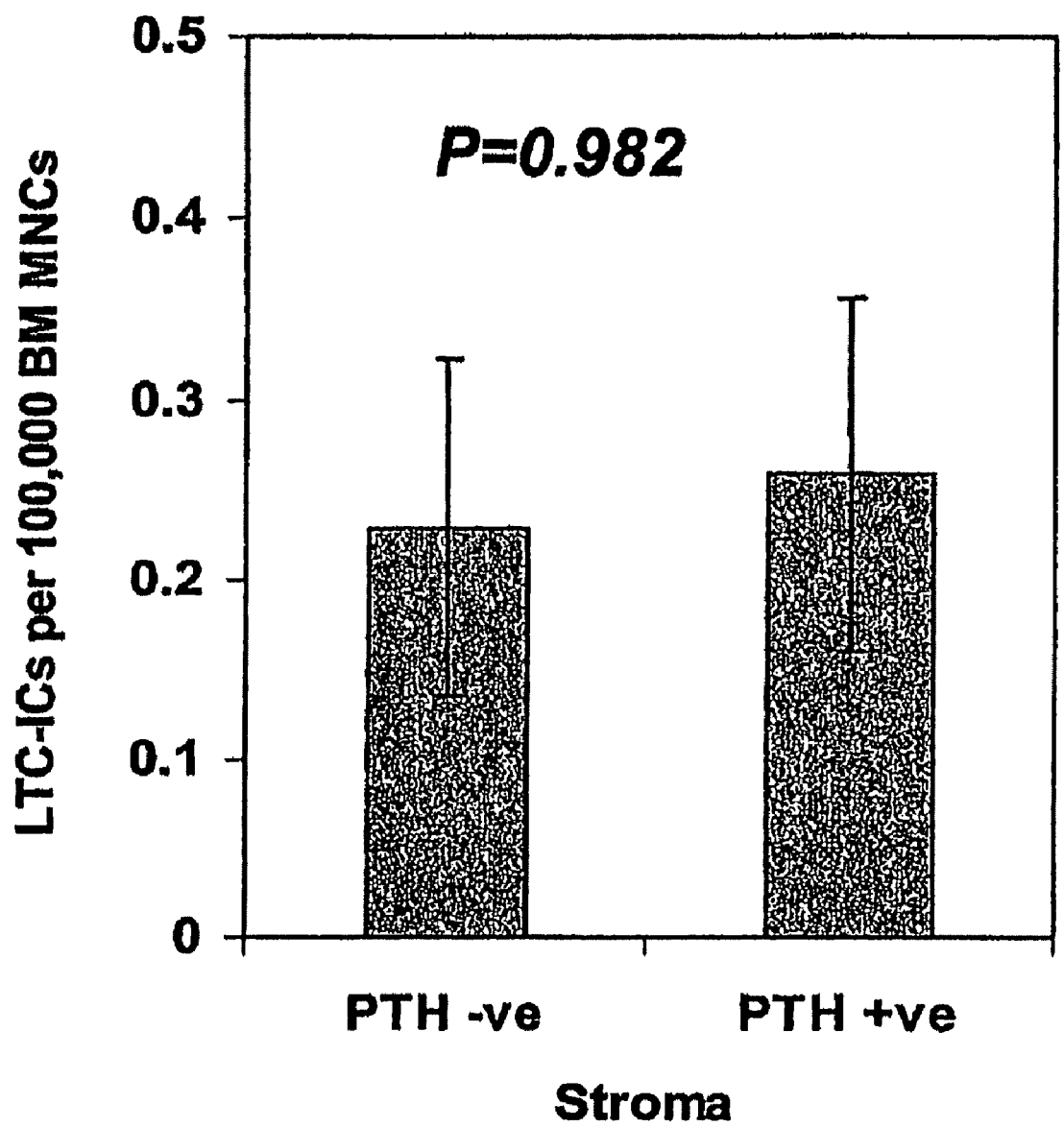
FIG. 4. Graph showing LTC-IC assay under non-contact culture conditions.

PPR transgenic osteoblastic cells highly express IL-6, SCF, and SDF-1. Immunohistochemistry was used to assess levels of Interleukin 6 (IL-6), kit ligand or Stem Cell Factor (SCF) and Stroma-derived Factor 1 (SDF-1) in the transgenic cells among the metaphyseal trabeculae. These cells have been previously shown by in situ hybridization to be a heterogeneous population of osteoblastic cells (Calvi et al., 2001), and immunohistochemistry for Osteopontin, a marker of osteoblastic cells, confirmed these data. In wild-type animals, only a few osteoblastic cells express these factors. In contrast, high levels of IL-6 were detected heterogeneously in the osteoblastic cells of transgenic animals. Expression of SDF-1 was diffuse, while SCF was present at high levels mainly in the more mature cells lining the trabeculae. To address whether diffusible cytokines could account for the effect on primitive cells, LTC-ICs were performed with a semi-permeable membrane separating feeder cells from BM MNCs (non-contact cultures) and noted abolition of benefit from the activated PPR(P=0.982, FIG. 4). These data indicate the requirement for cell-cell contact or direct primitive hematopoietic cell interaction with a niche cell or matrix component. SCF may be membrane bound as well as freely secreted. However, other candidate membrane restricted mediators of stem cell expansion were investigated.

Figure 3B:
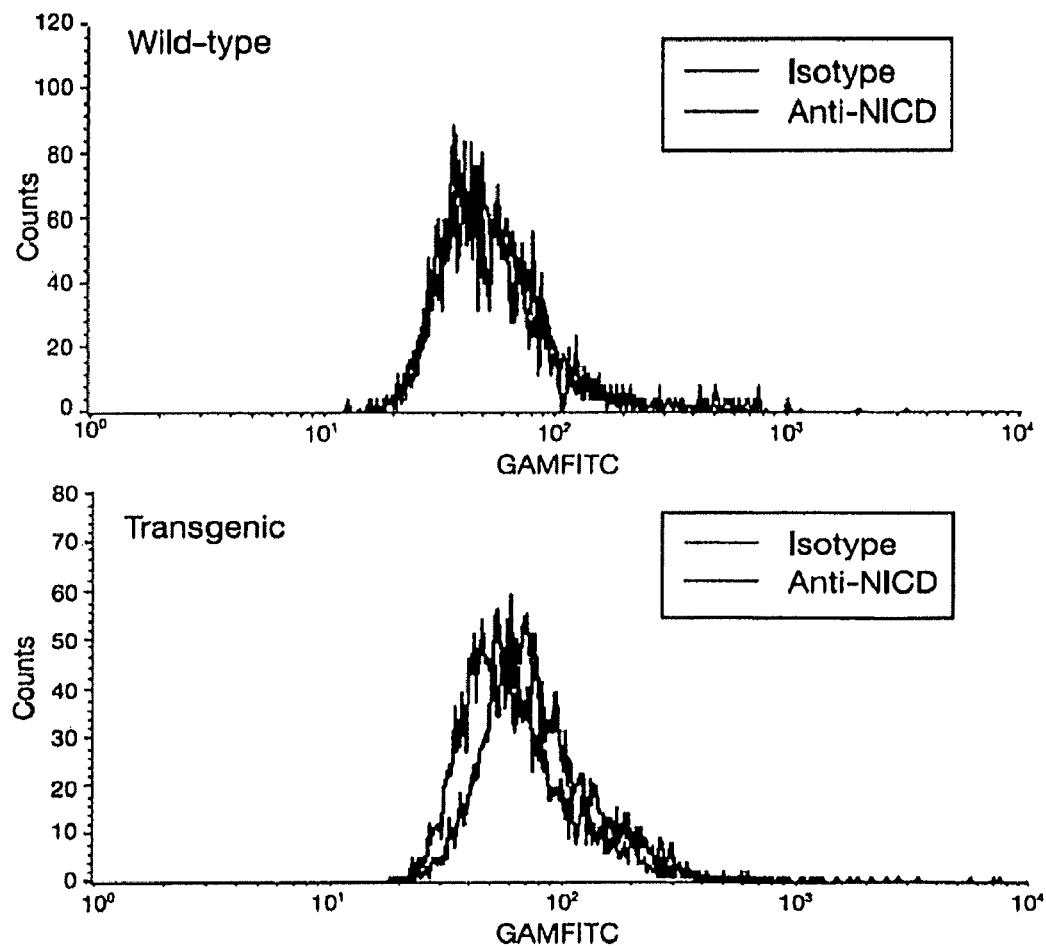

Transgenic osteoblastic cells produce high levels of the Notch ligand, Jagged1. The Notch signalling pathway, which regulates cell-fate specification in a wide variety of systems (Artavanis-Tsakonas et al, 1999, Science, 284:770-776), is thought to affect HSC self-renewal (Stier et al., 2002, Blood, 99:2369-2378; Varnum-Finney et al., 2003, Blood, 101:1784-1789; Varnum-Finney et al., 2000, Nat. Med., 6:1278-1281; Karanu et al., 2000, J. Exp. Med., 192:1365-1372; Karanu et al., 2001, Blood, 97:1960-1967). Manipulation of Notch signalling has been shown to increase stem cell numbers without expanding mature cells (Stier et al., 2002, Blood, 99:2369-2378; Karanu et al., 2000, J. Exp. Med., 192:1365-1372). Further, the Notch ligand Jagged1 has been shown to be expressed by marrow stromal cells (Karanu et al., 2000, J. Exp. Med., 192:1365-1372; Li et al., 1998, Immunity, 8:43-55) as well as murine osteoblasts (Pereira et al., 2002, J. Cell Biochem., 85:252-258). Notch and cytokine induced signalling pathways have been shown to have a combinatorial effect in regulating hematopoietic cell fate (Varnum-Finney et al., 2003, Blood, 101:1784-1789). It was therefore investigated whether Jagged1 protein levels were altered in the marrow of transgenic mice and observed by immunohistochemistry that overall levels of Jagged1 were dramatically increased. The cells expressing the Jagged1 were osteoblastic, as shown by their morphologic characteristics and staining with anti-Osteopontin antibody. To examine whether the hematopoietic stem cells responded to the increased expression of Jagged1 in the transgenic animals, the level of the Notch Intracellular Domain (NICD) was assessed in the lin$^-$Sca-1$^+$c-Kit$^+$ HSCs from wild-type and transgenic mice. The anti-NICD antibody has previously been shown to preferentially detect the activated intracellular form of Notch1 (Huppert et al., 2000, Nature, 405:966-970). Whereas wild-type mice had minimal staining for the NICD compared with isotype controls, lin$^-$ Sca-1$^+$c-Kit$^+$ cells from transgenic mice had a notable increase in the level of NICD (FIG. 3b). These data suggest a model in which activation of the PPR in the osteoblastic population increases their number and their overall production of Jagged1. This in turn may activate Notch1 on primitive hematopoietic cells resulting in expansion of the primitive cell compartment.

Example 4

In Vitro PTH Administration

Figure 5B:
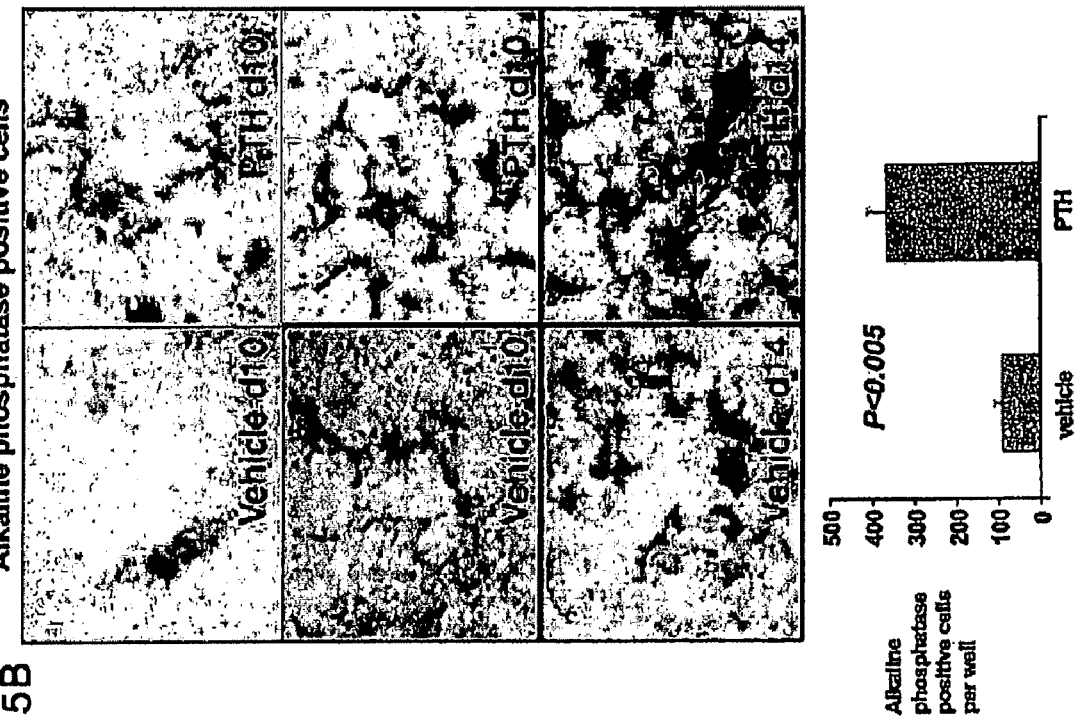
FIG. 5. a) Graph showing LTC-IC assay of C57B1/6 stroma expansion in the absence or presence of PTH. b) Photo showing alkaline phosphatase positive cells. c) Graph showing inhibition of LTC-IC in the presence or absence of PTH. d) Graph showing percentage of lin$^-$Sca-1$^+$c-Kit$^+$ cells in bone marrow in mock injected and PTH injected mice. e) Graph showing increase of LTC-ICs in bone marrow mononuclear cells in mock injected and PTH injected mice. f) Graph showing percentage of CD45.2$^+$ cells in bone marrow in mock injected and PTH injected mice. g) Graph showing CFU-Cs in bone marrow mononuclear cells in mock injected and PTH injected mice.
Figure 5A:
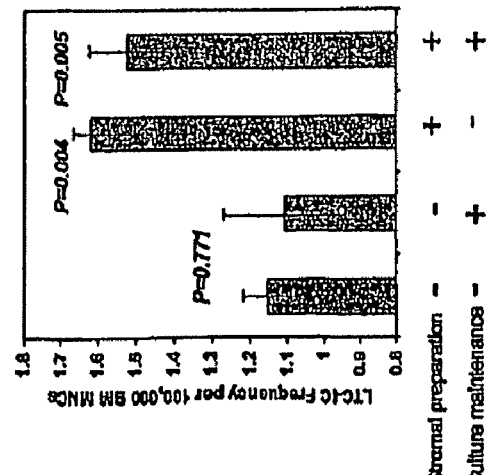
Figure 5C:
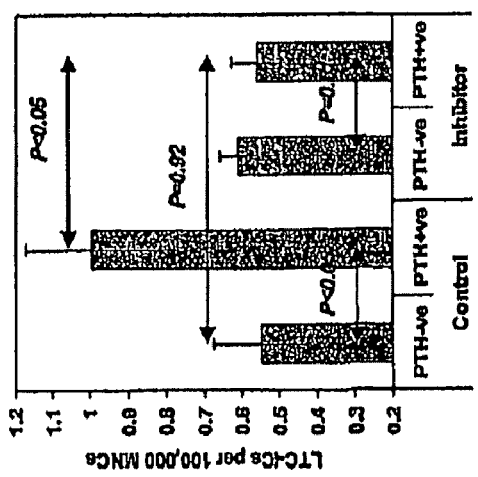

PTH treatment in vitro reproduces the col1-caPPR effect. Since the col1-caPPR mice represented a genetic means of activating a receptor that could also be activated by endogenous ligand, it was next tested whether the effects of col1-caPPR stroma could be recapitulated through exposure of wild type stroma to PTH. LTC-IC assays were performed using C57Bl/6 stroma expanded in vitro in the presence or absence of PTH, after which hematopoietic cells were introduced to the stroma in the presence or absence of PTH. When stroma was grown in medium containing PTH, it closely resembled the LTC-IC results using the col1-caPPR stroma, increasing LTC-IC (P=0.004, FIG. 5a). Of note, the effect was not seen using stromal cells that were expanded in the absence of PTH, or when PTH was added at the same time as the hematopoietic cells, suggesting an effect on the composition or activity of the stroma as it matures in vitro. To assess whether there was an increase in the osteoblastic cell number in the stromal cell cultures treated with PTH, alkaline phosphatase staining of primary murine stromal cell cultures treated with vehicle or PTH were performed. After 14 days, the cultures were confluent and heterogeneous, and there was an increase in alkaline positive cells in the PTH-treated cultures (FIG. 5b), verifying that activation of PPR induces an increase in the number of osteoblastic cells. To further assess whether the effects of PPR activation on primitive hematopoietic cells were due to Notch pathway activation, long term co-cultures in the presence or absence of a γ-secretase inhibitor capable of blocking Notch1 cleavage (Wolfe et al., 1999, Biochemistry, 38:4720-4727) were performed. Addition of the inhibitor reduced the supportive capacity of PTH treated stroma to baseline levels (FIG. 5c). Therefore, Notch1 activation is necessary for osteoblastic cell induced increases in primitive hematopoietic cells. Taken together, these results further support the model that PPR activation can increase osteoblastic cells resulting in Notch1 mediated expansion of primitive hematopoietic cells.

Example 5

In Vivo PTH Administration

Figure 5D:
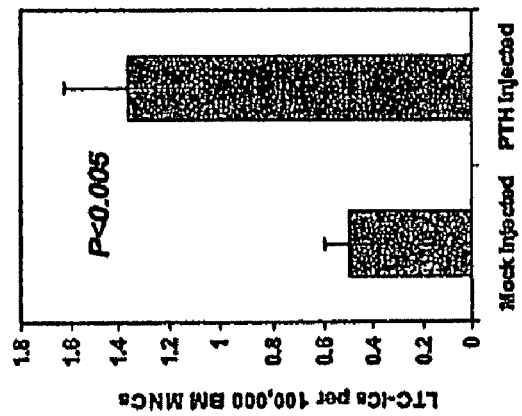
Figure 5F:
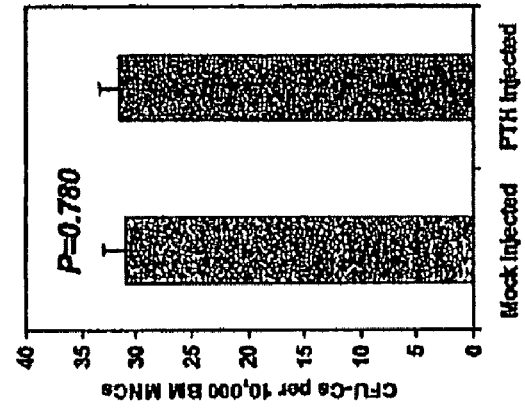
Figure 5E:
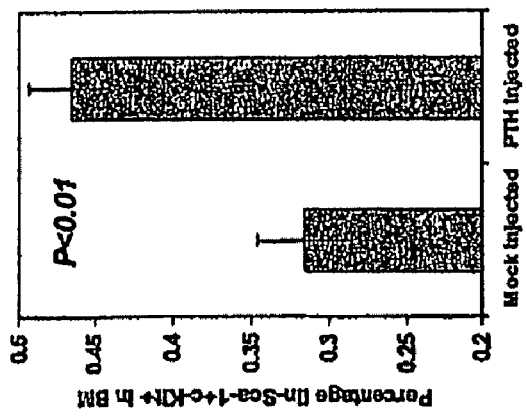
Figure 5G:
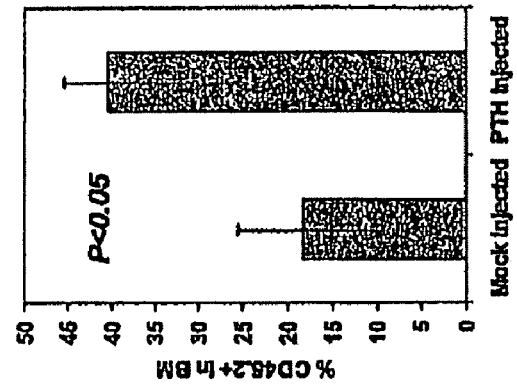

Intermittent PTH treatment of normal mice. As treatment of stromal cells with PTH led to an increase in the ability of the stromal cell population to support hematopoietic stem cells, it was investigated whether these effects could be recapitulated in vivo. Wild-type C57Bl/6 mice were injected daily with PTH using an intermittent dosing schedule known to increase osteoblasts, and the frequencies of LTC-ICs in the bone marrow were measured. Whereas a two week PTH treatment period did not result in any significant increase in the hematopoietic stem cell population, treatment of mice for four weeks with PTH resulted in a significant increase in the hematopoietic stem cells over mock injected mice. By four weeks, a significant difference was noted with PTH treated mice having a higher frequency and absolute number of lin$^-$ Sca-1$^+$c-Kit$^+$ compared with mock treated controls (P=<0.01, FIG. 5d). Further, the limit dilution LTC-IC assay demonstrated an increase in stem-like cells (P=<0.005, FIG. 5e). To further define that functional stem cells were increased after PTH treatment, an in vivo assay of competitive transplantation into secondary recipients was used and a >2-fold increase in HSCs was documented (P=<0.05, FIG. 5f). These data provide evidence for an increase in HSCs induced by PTH and also serve to validate the reasonable comparability of the in vitro and in vivo assays used in these studies. Consistent with observations in the transgenic animals, PTH treatment did not affect the level of hematopoietic progenitors as assessed by CFU-C assay (P=0.780, FIG. 5g). Therefore, pharmacological activation of PPR increased stem cell number, but appeared to do so without a broad hematopoietic cell expansion. These data are most consistent with HSC expansion by enhanced self-renewal, a phenomenon known to result from Notch activation. Of note, there was no evidence of hypercalcemia by serum calcium measurements of the PTH treated animals.

PTH administration in vivo following bone marrow transplantation. Assessing whether PPR stimulation could affect models relevant to the clinical use of stem cells in humans, the impact of PTH administration on animals undergoing myeloablation and bone marrow transplantation was assessed. Limiting numbers of bone marrow derived donor cells were used to mimic a setting of therapeutic need. Survival rate at 30 days in control mice receiving mock injections after bone marrow transplantation was 40%. In sharp contrast, animals receiving pulse dosing of PTH had markedly improved outcomes with 100% survival (FIG. 6).

Example 6

Preventing Chemotherapic Damage with PTH

PTH provides a protective effect during a course of G-CSF and cyclophosphamide therapy. Cyclophosphamide is used as a chemotherapeutic agent in the treatment of hematological malignancies. Due to the myelotoxic effects of cyclophosphamide on the bone marrow, granulocyte colony-stimulating factor ("G-CSF") is typically administered to augment the recovery from the chemotherapy-induced neutropenia. However, treatment with G-CSF following administration of cyclophosphamide is known to reduce the hematopoietic stem cell (HSC) sub-population of cells in the bone marrow. The protective effect of PTH administration during a course of G-CSF and cyclophosphamide therapy was observed as described herein.

PTH administration in vivo. Wild-type C57Bl/6 mice were treated with 5 mg of cyclophosphamide (Day 1). The day following injection of cyclophosphamide, mice received no treatment or were treated for 8 days with G-CSF (5 μg/day), 11 days with PTH (80 μg/kg/day) or a combination of G-CSF plus PTH. Mice that received a combination of both G-CSF and PTH received G-CSF treatment for 8 days and PTH treatment for 11 days. Following this treatment protocol, mice were injected with cyclophosphamide on Day 15 and treated with G-CSF, PTH or G-CSF and PTH as described above. The treatment protocol was then repeated for two subsequent cycles, as outlined in FIG. 7.

Complete blood count analysis. During the course of the four treatment cycles, peripheral blood complete blood count (CBC) analysis was performed every 2 to 3 days. This analysis involved the collection of 100 µl of peripheral blood from the tail vein of the mice, which was subsequently analyzed on a HEMAVET 850FS (Drew Scientific). To avoid any deleterious effects from repeated tail bleeds, each individual mouse was only bled once per week.

Assays for hematopoietic stem cells. At the end of the four-cycle treatment with cyclophosphamide and G-CSF/PTH, the bone marrow was removed from the treated mice and competitive transplants into B6.SJL mice were performed to measure the maintenance of the HSC pool in the bone marrow. This involved mixing $5 \times 10^5$ BM cells from the treated C57B1/6 mice (CD45.2) with $2.5 \times 10^5$ BM cells from the B6.SJL mice (CD45.1). These cells were then injected into lethally irradiated B6.SJL mice. Eighteen weeks following injection of the cells, peripheral blood was collected from the mice and the relative contribution of the HSCs from the treated animals was measured by flow cytometry for the CD45.2$^+$ cells. To assess the ability of the HSCs to be mobilized into the peripheral circulation, one week following treatment mice were mobilized with G-CSF (5 µg/day) for 5 days. Peripheral blood (300 µl) was collected from these mice and mixed with $2.5 \times 10^5$ BM cells from a B6.SJL mouse. These cells were injected into a lethally irradiated B6.SJL host. Eighteen weeks following injection of the cells, peripheral blood was collected from the mice and the relative contribution of the HSCs from the treated animals was measured by flow cytometry for the CD45.2$^+$ cells.

Administration of PTH does not alter the hematopoietic response following chemotherapy, with or without G-CSF support. Analysis of the peripheral blood in terms of white blood count (WBC), neutrophils count (NE), hemoglobin concentration (Hb) and platelet count (Plt) during the 8-week chemotherapy treatment period is shown in FIG. 7, A-D. Mice that received G-CSF demonstrated significant increases in their WBC and NE counts following chemotherapy that was not altered by the addition of PTH treatment. Similarly, mice that did not receive G-CSF demonstrated no differences in their hematological response to chemotherapy whether they received PTH or not. The Hb and Plt responses were not significantly different between any of the treatment groups.

Figure 7B:
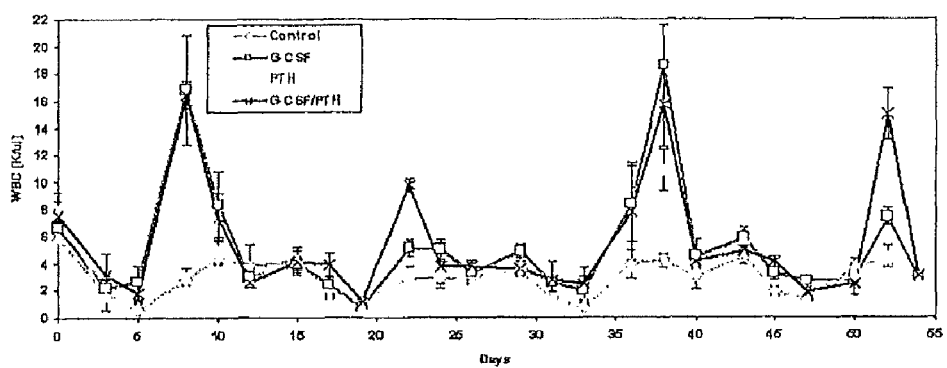
Figure 7C:
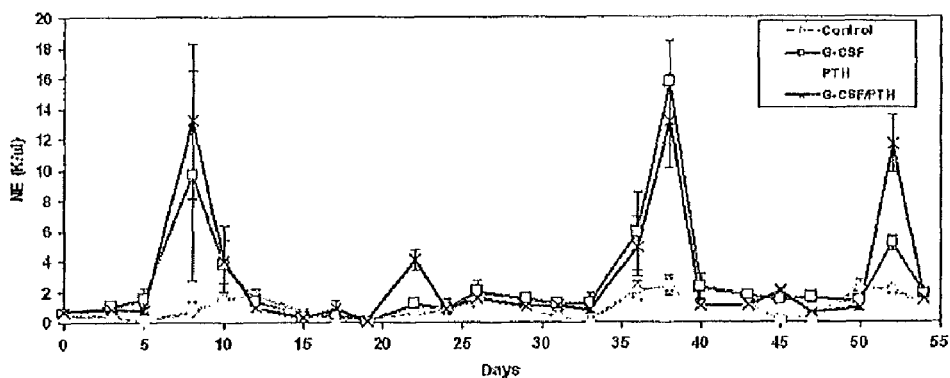
Figure 7D:
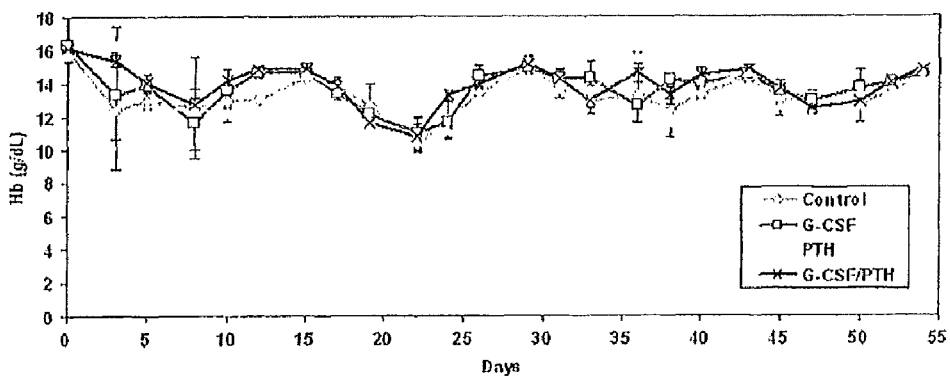
Figure 7E:
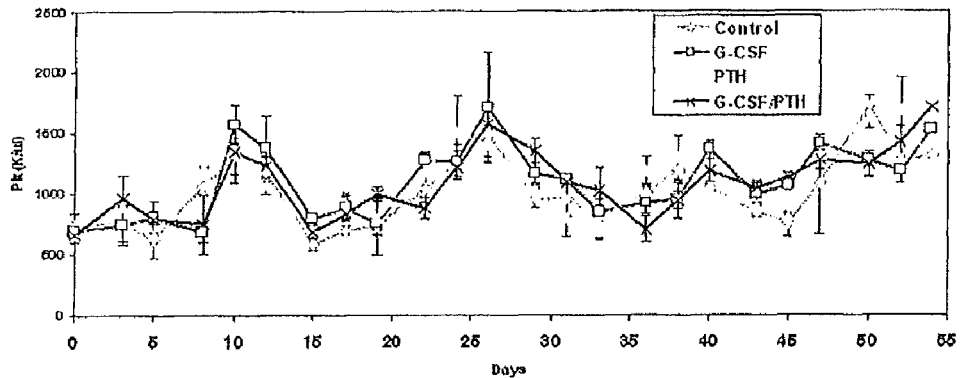
Figure 7F:
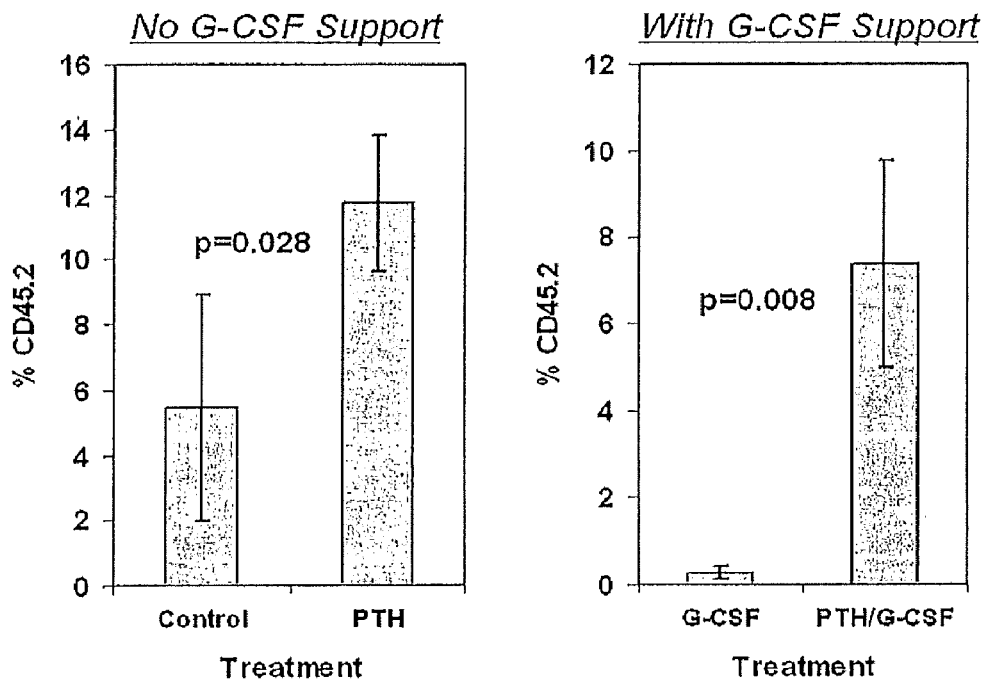
Figure 7G:
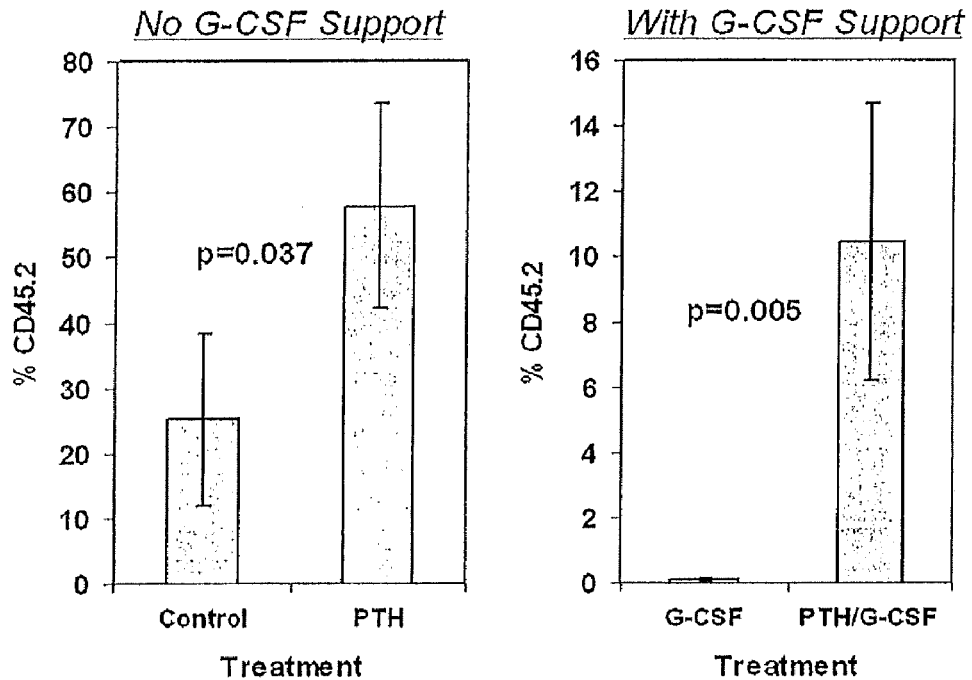

Administration of parathyroid hormone (PTH) results in a preservation of the HSC pool following chemotherapy. Analysis of the HSC pool in the bone marrow following chemotherapy demonstrated that PTH treatment increased the HSC pool in the non-G-CSF treated animals following myelotoxic chemotherapy (FIG. 7E). In the animals treated with G-CSF alone, there was a significant depletion of the HSC pool, as has been described by others. However, the concurrent treatment with PTH led to retention of the HSC pool (FIG. 7E). Analysis of the mobilization of the HSCs into the peripheral circulation with G-CSF demonstrated that in mice that did not receive supportive G-CSF therapy during the myeloablative chemotherapy there was mobilization of HSCs into the circulation, which was increased with prior PTH treatment (FIG. 7F). However, mice that received supportive growth factor therapy alone showed little to no mobilization of the HSCs into the peripheral circulation, which was partially reversed by the concurrent treatment with PTH (FIG. 7F).

Taken together, these studies demonstrate that targeting the niche can protect, or even expand the HSC pool in the bone marrow during myelotoxic chemotherapy. This is especially evident when growth factor supportive therapy is used in conjunction with chemotherapy. These results illustrate the usefulness of PTH therapy in protection of hematopoietic stem cells during myelotoxic chemotherapy.

Example 7

Kinetics of Leukemia Cell Engraftment, Growth and Maturation

Figure 9A:
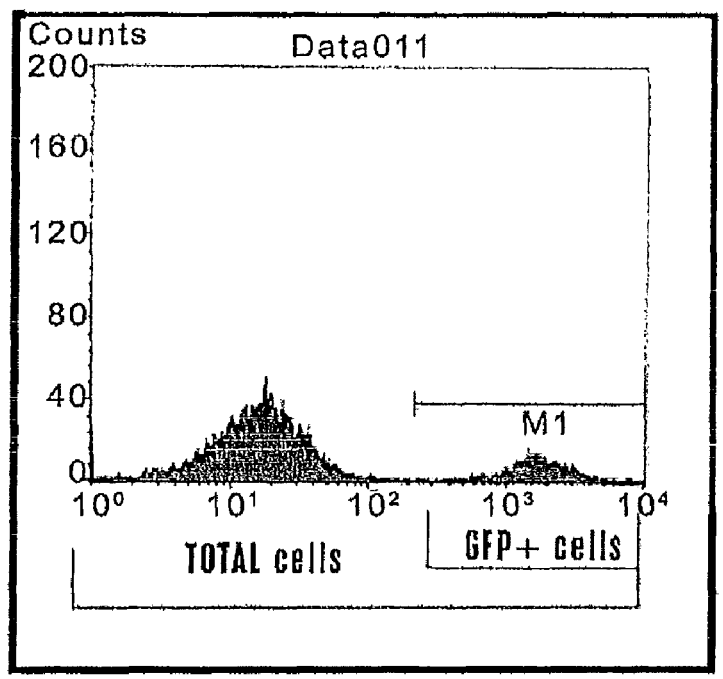
FIG. 9. a) Graph showing tracking of GFP+ cells in total cell population. b) Bar graphs showing percent leukemia (GFP+) cells over time in the marrow (above) and blasts per $10^4$ over time in the periphery.

The kinetics of leukemia cell engraftment, growth, and maturation were studied in normal mice. In an effort to analyze the growth and fate of C-1498 leukemia cells transplanted into mice, the cells were transduced with a retrovirus expressing GFP (C-1498/GFP). This allows easy tracking of these cells in vivo using GFP as a marker (FIG. 9a). The acute myelogenous leukemia cell line C-1498, a spontaneously-arising acute myelomonocytic leukemia derived from C57/BL6 (H2-b) mice, is easily transplantable, can be cultured in vitro, and infected with retroviruses.

Figure 9B:
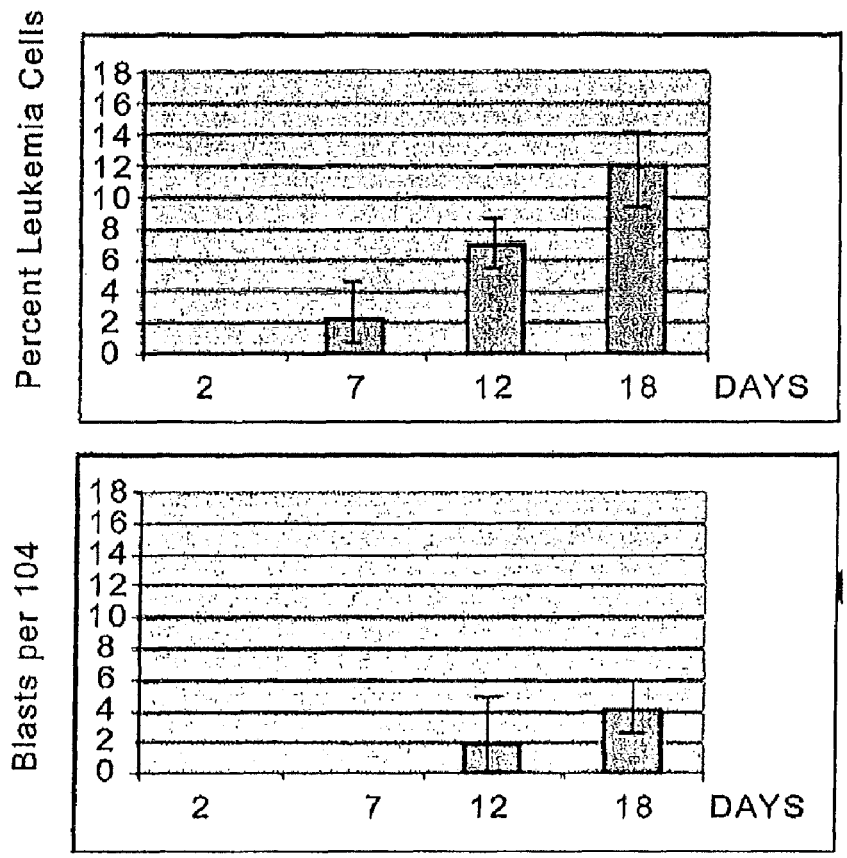

As shown in FIG. 9b, upon transplantation of 50,000 C-1498/GFP cells into mice, the number of GFP-positive cells in the marrow was 2% at 2 days, 8% by 7 days, and 12% by 18 days. At 7 days, there were no blasts in the periphery. However, at 15-18 days, blasts began to reliably appear in peripheral blood. At 22 days, most mice were moribund.

Figure 10A:
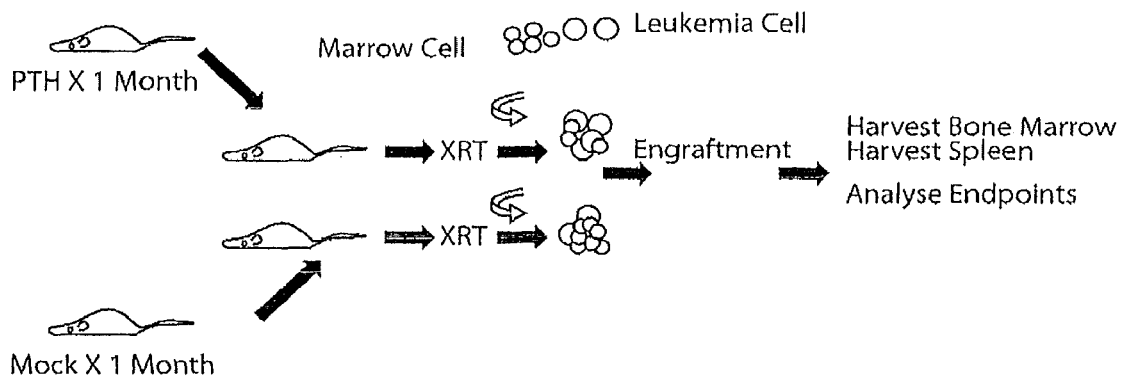
FIG. 10. a) Schematic depiction of leukemia outgrowth in "niche-stimulated" animal study. b) Bar graph showing percent GFP+ cells scored after bone marrow transplant and harvest of afore-mentioned study. c) Histological images of 10-micron bone sections from transplanted mock-treated vs. PTH-treated animals.
Figure 10B:
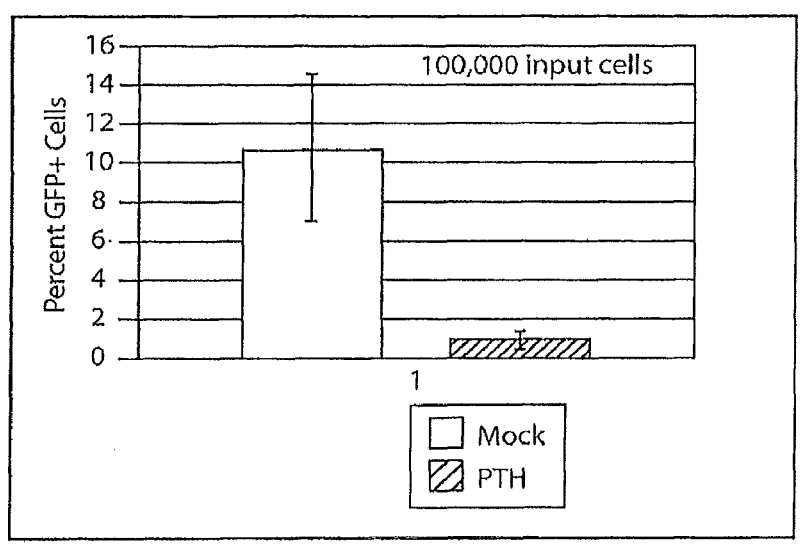
Figure 10C:
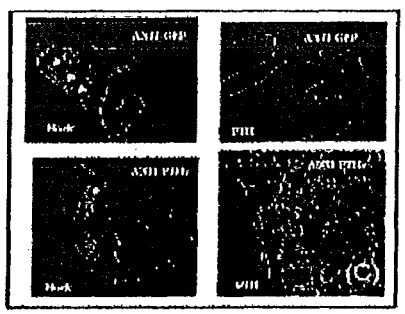

Attention was subsequently directed to determining how activation of the stem cell niche with PTH might affect leukemia growth and maturation. To investigate the kinetics of leukemia outgrowth in "niche-stimulated" animals, animals were pre-stimulated with PTH at 80 µg/kg/day (versus saline alone) for one month. Mice were then lethally irradiated at 10 Gray, and then transplanted with 50,000 leukemia cells (GFP+) and $1 \times 10^6$ normal bone marrow cells (GFP−) (FIG. 10a). At 15 days post-transplantation, bone marrow was harvested, and, then, GFP-positive cells were scored as percentage and in absolute number. Since the absolute number of total cells was not statistically different between both groups, only the percentage figures are shown in FIG. 10b, left panel. Of note, in 3 of 3 experiments, the number of GFP-positive leukemia initiating cells was markedly reduced in the PTH treated animals.

To obtain a histological correlate of these results, 10 micron bone sections were cut from transplanted mock-treated and PTH-treated animals. In mock-treated animals, osteoblasts and osteoprogenitors, identified at PTH-receptor positive cells, were found lining the endostial surfaces of bone. In contrast, in PTH-treated animals, PTH-r positive cells had migrated extensively into the marrow. Concomitantly, while GFP-positive leukemia cells were found in mock-treated animals (particularly along the bone surfaces), GFP-positive cells were markedly reduced in PTH-treated animals (FIG. 10b, right panel).

Figure 11:
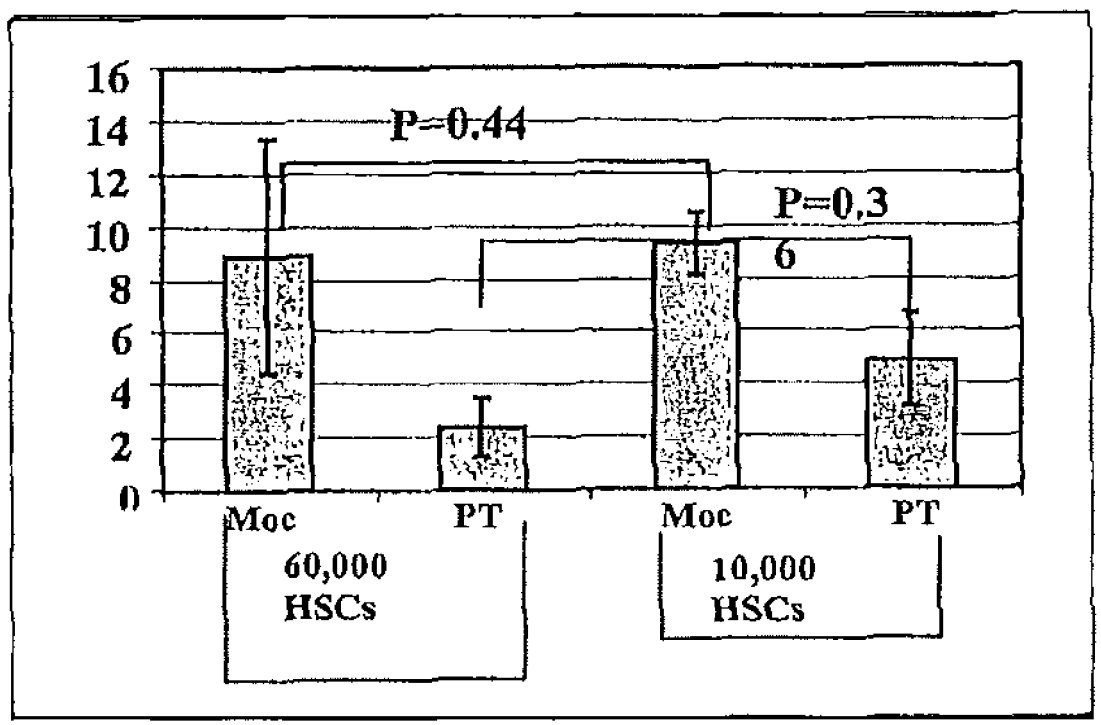
FIG. 11. Bar graph showing unchanged leukemia inhibition effect as observed for mock-treated vs. PTH-treated animals with a six-fold increase in HSCs and with no such increase.

The ability of PTH treatment to alter the relative proportion of normal to leukemia initiating stem cells may involve several mechanisms. First, the cells may compete for niche spaces that are different and the PTH 'expanded' niches may not have a proportionate likelihood of supporting leukemic and normal stem cells. The ability to modify the relative abundance of normal to leukemic cells by increasing the ratio of normal to leukemic cells suggests that such a mechanism may apply. Differential production of normal cells over leukemic cells in a PTH treated animal did not seem to be the case as kinetics of normal hematopoiosis did not change (FIG. 11). However, differential sensitivity to an inhibiting signal may be a potential mechanism as was further tested.

Figure 12A:
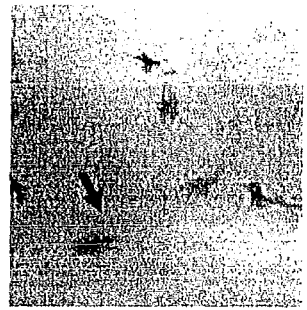
FIG. 12. a) Schematic depiction of osteoblast/C1498/GFP leukemia cell co-culture experiment. b) FACS plot showing osteoblasts isolated on the basis of CD45 and PTH receptor. c) Alkaline phosphatase staining of CD45$^-$, PTH receptor$^+$ population of osteoblasts. d) Further schematic depiction of osteoblast/C1498/GFP leukemia cell co-culture experiment. e) Bar graph showing total cell number vs. fibroblasts alone and fibroblasts with osteoblasts.
Figure 12B:
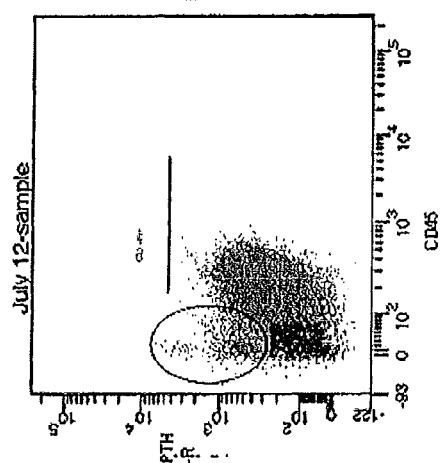
Figure 12C:
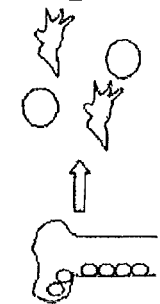

Since PTH did not directly affect leukemic cells in vitro, the osteoblast-leukemic cell interaction was further characterized. Osteoblasts and C 1498/GFP leukemia cells were co-cultured. The scheme for this experiment is shown in FIG. 12a. Bone marrow was harvested from wild-type and Col A-PPR* mice, and the total cellular content was cultured for 10 days in vitro. After 10 days of culture, cells were dissociated into single cell suspension. Osteoblasts express the PTH receptor, but not CD45, a universal marker for hematopoietic cells. To purify osteoblasts from the in vitro cultures, CD 45-, PTH receptor+fraction was isolated by FACS (FIG. 12b). This population was subsequently stained by Alkaline Phosphatase and shown to be Alk+, indicating that these were purified osteoblasts (FIG. 12c).

Figure 12D:
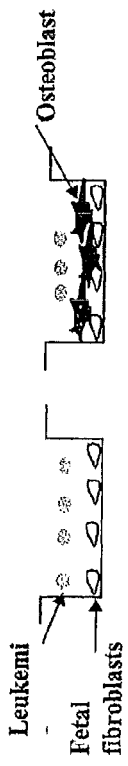
Figure 12E:
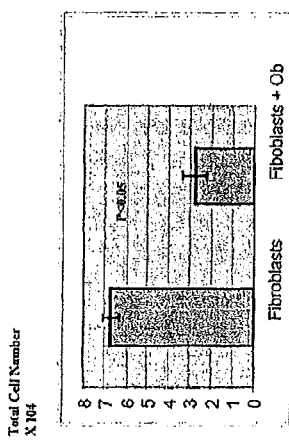

After the isolation of osteoblasts, osteoblasts and C1498/GFP leukemia cells were co-cultured (FIG. 12d). 3 days after co-culture, the fraction of GFP+ positive cells and total cells was counted by FACS analysis again (FIG. 12e). Of note, there was a significant reduction of leukemic cells in the osteoblast co-cultures compared to the control cultures (fibroblast alone). In addition, leukemic clone sizes in osteoblast cultures were found to be smaller (1-2 cells), while clone sizes in fibroblast cultures were 5-8 cells, suggesting that leukemic cells have reduced capacity to expand in the presence of osteoblasts.

To further investigate the phenomenon of osteoblast-mediated leukemia cell inhibition (as demonstrated by the preliminary in vitro experiments described herein), a candidate molecule approach was taken. Osteopontin (OPN), a molecule secreted by osteoblasts, is a key regulator of the normal hematopoietic stem cell niche. In particular, OPN appears to limit the number of early primitive hematopoietic cells (Stier, S. et al. (2005) J. Exp. Med. 201(11):1781-91).

To investigate the role of OPN as a candidate molecule, it was explored whether recombinant OPN is sufficient to reproduce the growth inhibition of leukemia cells in vitro. To this end, C-1498/GFP cells were cultured in wells with either (a) no OPN, (b) with 5 and 10 ug/ml of OPN. Of note, OPN was found sufficient to reproduce the inhibition of leukemia cell growth in this system (FIG. 13b). Staining with Annexin further revealed that the effect was due to OPN mediated growth inhibition rather than accelerated apoptosis (FIG. 13a). It was therefore concluded that recombinant osteopontin is sufficient to limit leukemic cell expansion. The relative ability of OPN to limit primitive cell expansion was greater in leukemic compared to normal cells. Given that PTH increases osteoblast production of OPN, it is likely that OPN participates in the preferential support of normal over leukemic cells in vivo with PTH stimulation of the stem cell niche.

In view of the results presented herein, it was concluded that PTH/PTHrP receptor stimulation with PTH and its analogues can affect the relative balance of normal and malignant cell function, thereby changing the phenotype of the malignancy to the benefit of the patient. Accordingly, leukemic and pre-leukemic conditions (e.g., myelodysplastic syndrome) characterized by the progressive domination of abnormal cells can be ameliorated or eradicated by that PTH/PTHrP receptor stimulation. Given that PTH receptor is on many stromal cell components of many tissues, it may be that PTH stimulation is capable of altering normal and malignant cell ratios in many tumor types.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

We claim:

1. A method for increasing the ratio of normal to abnormal hematopoietic cells in a subject in need thereof, the method comprising:
   contacting a population of cells expressing a PTH/PTHrP receptor in the subject with an agent that activates the PTH/PTHrP receptor in an amount and for a duration effective to expand a population of hematopoietic stem or progenitor cells, thereby increasing the ratio of normal to abnormal hematopoietic cells in the subject, wherein the subject is a bone marrow donor who has donated bone marrow, is a bone marrow donor who has yet to donate bone marrow, is a bone marrow donor transplant recipient, has hematopoietic progenitor cells under environmental stress, has anemia, has a reduced level of immune cell function compared to a normal subject, has an immune system deficiency, has received chemotherapy or radiation therapy for cancer, will receive chemotherapy or radiation therapy for cancer, has a disorder characterized by a lack of functional immune cells, has received an immuno-suppressive drug, will receive an immuno-suppressive drug, is receiving an immuno-suppressive drug or is a stem cell donor.

2. The method of claim 1, wherein the population of cells expressing a PTH/PTHrP receptor are present in the immediate vicinity of the population of hematopoietic stem or progenitor cells.

3. The method of claim 1, wherein the population of cells expressing a PTH/PTHrP receptor are selected from the group consisting of from osteoblasts, lymphoreticular stromal cells, and a mixture of osteoblasts and lymphoreticular stromal cells.

4. The method of claim 1, wherein the abnormal cells are leukemic cells.

5. The method of claim 4, wherein the leukemic cells are lymphoblastic.

6. The method of claim 1, wherein the abnormal cells are pre-leukemic cells.

7. The method of claim 6, wherein the pre-leukemic cells are myelodysplasic cells.

8. The method of claim 1, wherein the agent that activates the PTH/PTHrP receptor is PTH, a PTH analogue, or a PTH/PTHrP receptor agonist.

9. The method of claim 1, wherein the subject has or is at risk of having leukemia.

10. The method of claim 9, wherein the leukemia is chronic.

11. The method of claim 10, wherein the chronic leukemia is chronic myeloid, chronic myelogenous or chronic granulocytic leukemia.

12. The method of claim 9, wherein the leukemia is acute.

13. The method of claim 12, wherein the acute leukemia is acute lymphoblastic leukemia or acute nonlymphoblastic leukemia.

14. The method of claim 1, wherein the agent is administered to the subject at least five times per week for four weeks.

* * * * *